(12) United States Patent
Kuroda et al.

(10) Patent No.: US 8,863,748 B2
(45) Date of Patent: Oct. 21, 2014

(54) ENDOSCOPIC SURGICAL OPERATION METHOD

(75) Inventors: Noriko Kuroda, Tokyo (JP); Takayasu Mikkaichi, Tokyo (JP); Kosuke Motai, Tokyo (JP); Kazushi Murakami, Tokyo (JP); Manabu Miyamoto, Tokyo (JP); Shotaro Takemoto, Tokyo (JP); Satoko Suzuki, Tokyo (JP)

(73) Assignee: Olympus Medical Systems Corp. (JP)

( * ) Notice: Subject to any disclaimer, the term of this patent is extended or adjusted under 35 U.S.C. 154(b) by 1038 days.

(21) Appl. No.: 12/183,184

(22) Filed: Jul. 31, 2008

(65) Prior Publication Data

US 2010/0030019 A1    Feb. 4, 2010

(51) Int. Cl.
| A61B 19/00 | (2006.01) |
| A61B 1/00 | (2006.01) |
| A61B 17/04 | (2006.01) |
| A61B 17/06 | (2006.01) |
| A61B 17/00 | (2006.01) |

(52) U.S. Cl.
CPC ......... *A61B 17/0401* (2013.01); *A61B 17/0469* (2013.01); *A61B 17/0482* (2013.01); *A61B 2017/06052* (2013.01); *A61B 2017/00818* (2013.01); *A61B 2017/0417* (2013.01); *A61B 2017/00296* (2013.01)
USPC .......................................... 128/898; 600/106

(58) Field of Classification Search
USPC .......... 600/106, 104, 129–130, 153; 128/898; 606/139–150
See application file for complete search history.

(56) References Cited

U.S. PATENT DOCUMENTS

| 4,245,624 A | * | 1/1981 | Komiya ................. 600/106 |
| 4,706,655 A | * | 11/1987 | Krauter ................. 600/106 |
| 5,403,326 A | * | 4/1995 | Harrison et al. ........ 606/139 |
| 5,573,494 A | * | 11/1996 | Yabe et al. ............. 600/121 |
| 5,665,109 A | * | 9/1997 | Yoon .................... 606/232 |
| 5,792,153 A | * | 8/1998 | Swain et al. ........... 606/144 |
| 5,868,760 A | * | 2/1999 | McGuckin, Jr. ........ 606/139 |
| 5,947,983 A | * | 9/1999 | Solar et al. ............. 606/144 |
| 5,947,994 A | * | 9/1999 | Louw et al. ............ 606/200 |

(Continued)

FOREIGN PATENT DOCUMENTS

| JP | S61-124604 | 8/1986 |
| JP | 2004-041733 | 2/2004 |

(Continued)

OTHER PUBLICATIONS

Extended European Search Reported dated Oct. 5, 2009 in corresponding European Patent Application No. EP 09 00 9890 (in English language).

(Continued)

*Primary Examiner* — Andrew Iwamaye
(74) *Attorney, Agent, or Firm* — Ostrolenk Faber LLP

(57) ABSTRACT

Endoscopic surgical operation method includes: a step of lifting a living tissue including an diseased tissue located distally relative to an operation channel of an endoscope inserted through a natural orifice; a step of suturing a proximal region and a distal region of the living tissue positioned basal relative to the diseased tissue lifted by a suturing means section projecting distally from the operation channel of the endoscope after the lifting; and a step of resecting the living tissue between the sutured regions and the diseased tissue endoscopically after suturing the proximal region and the distal region of the living tissue surrounding the diseased tissue.

13 Claims, 23 Drawing Sheets

(56) References Cited

U.S. PATENT DOCUMENTS

| | | | |
|---|---|---|---|
| 6,119,913 A * | 9/2000 | Adams et al. | 227/176.1 |
| 6,173,715 B1 * | 1/2001 | Sinanan et al. | 128/899 |
| 6,178,968 B1 * | 1/2001 | Louw et al. | 128/898 |
| 6,280,702 B1 * | 8/2001 | Carter et al. | 424/9.1 |
| 6,302,311 B1 * | 10/2001 | Adams et al. | 227/176.1 |
| 6,352,503 B1 * | 3/2002 | Matsui et al. | 600/104 |
| 6,398,795 B1 * | 6/2002 | McAlister et al. | 606/139 |
| 6,458,074 B1 * | 10/2002 | Matsui et al. | 600/106 |
| 6,527,753 B2 * | 3/2003 | Sekine et al. | 604/264 |
| 6,551,330 B1 * | 4/2003 | Bain et al. | 606/144 |
| 6,599,496 B2 * | 7/2003 | Carter et al. | 424/9.1 |
| 6,605,033 B1 * | 8/2003 | Matsuno | 600/107 |
| 6,605,078 B2 * | 8/2003 | Adams | 606/1 |
| 6,773,440 B2 * | 8/2004 | Gannoe et al. | 606/142 |
| 6,808,491 B2 * | 10/2004 | Kortenbach et al. | 600/104 |
| 6,824,509 B2 * | 11/2004 | Yamaya et al. | 600/106 |
| 6,827,683 B2 * | 12/2004 | Otawara | 600/123 |
| 6,908,427 B2 * | 6/2005 | Fleener et al. | 600/104 |
| 6,960,162 B2 * | 11/2005 | Saadat et al. | 600/114 |
| 6,971,988 B2 * | 12/2005 | Orban, III | 600/104 |
| 6,986,737 B2 * | 1/2006 | Suzuki et al. | 600/106 |
| 7,060,025 B2 * | 6/2006 | Long et al. | 600/106 |
| 7,063,661 B2 * | 6/2006 | Okada | 600/127 |
| 7,063,710 B2 * | 6/2006 | Takamoto et al. | 606/144 |
| 7,063,715 B2 * | 6/2006 | Onuki et al. | 606/220 |
| 7,087,010 B2 * | 8/2006 | Ootawara et al. | 600/104 |
| 7,122,002 B2 * | 10/2006 | Okada | 600/127 |
| 7,156,857 B2 * | 1/2007 | Pasricha et al. | 606/148 |
| 7,235,089 B1 * | 6/2007 | McGuckin, Jr. | 606/167 |
| 7,306,613 B2 * | 12/2007 | Kawashima et al. | 606/148 |
| 7,326,221 B2 * | 2/2008 | Sakamoto et al. | 606/139 |
| 7,334,718 B2 * | 2/2008 | McAlister et al. | 227/175.1 |
| 7,341,554 B2 * | 3/2008 | Sekine et al. | 600/106 |
| 7,341,555 B2 * | 3/2008 | Ootawara et al. | 600/106 |
| 7,361,180 B2 * | 4/2008 | Saadat et al. | 606/139 |
| 7,416,554 B2 * | 8/2008 | Lam et al. | 606/153 |
| 7,571,729 B2 * | 8/2009 | Saadat et al. | 128/898 |
| 7,588,580 B2 * | 9/2009 | Okada | 606/113 |
| 7,618,426 B2 * | 11/2009 | Ewers et al. | 606/139 |
| 7,637,905 B2 * | 12/2009 | Saadat et al. | 606/1 |
| 7,662,089 B2 * | 2/2010 | Okada et al. | 600/113 |
| 7,704,264 B2 * | 4/2010 | Ewers et al. | 606/151 |
| 7,722,631 B2 * | 5/2010 | Mikkaichi et al. | 606/144 |
| 7,736,372 B2 * | 6/2010 | Reydel et al. | 606/148 |
| 7,736,374 B2 * | 6/2010 | Vaughan et al. | 606/153 |
| 7,736,378 B2 * | 6/2010 | Maahs et al. | 606/232 |
| 7,744,613 B2 * | 6/2010 | Ewers et al. | 606/153 |
| 7,918,845 B2 * | 4/2011 | Saadat et al. | 606/1 |
| 7,951,157 B2 * | 5/2011 | Gambale | 606/144 |
| 7,955,340 B2 * | 6/2011 | Michlitsch et al. | 606/139 |
| 7,988,618 B2 * | 8/2011 | Mikkaichi et al. | 600/114 |
| 8,083,666 B2 * | 12/2011 | Adams | 600/104 |
| 8,430,808 B2 * | 4/2013 | Piskun | 600/104 |
| 2002/0091303 A1 * | 7/2002 | Ootawara et al. | 600/106 |
| 2003/0009085 A1 * | 1/2003 | Arai et al. | 600/127 |
| 2003/0040657 A1 * | 2/2003 | Yamaya et al. | 600/107 |
| 2003/0139752 A1 * | 7/2003 | Pasricha et al. | 606/139 |
| 2003/0171760 A1 * | 9/2003 | Gambale | 606/139 |
| 2003/0176766 A1 * | 9/2003 | Long et al. | 600/106 |
| 2003/0176767 A1 * | 9/2003 | Long et al. | 600/106 |
| 2003/0181924 A1 * | 9/2003 | Yamamoto et al. | 606/144 |
| 2003/0195529 A1 * | 10/2003 | Takamoto et al. | 606/145 |
| 2003/0208209 A1 * | 11/2003 | Gambale et al. | 606/144 |
| 2004/0034278 A1 * | 2/2004 | Adams | 600/127 |
| 2004/0039249 A1 * | 2/2004 | Shiro et al. | 600/101 |
| 2004/0138682 A1 * | 7/2004 | Onuki et al. | 606/144 |
| 2004/0158125 A1 * | 8/2004 | Aznoian et al. | 600/106 |
| 2004/0162568 A1 * | 8/2004 | Saadat et al. | 606/153 |
| 2004/0210111 A1 * | 10/2004 | Okada | 600/127 |
| 2004/0225183 A1 * | 11/2004 | Michlitsch et al. | 600/106 |
| 2004/0225305 A1 * | 11/2004 | Ewers et al. | 606/153 |
| 2004/0242960 A1 * | 12/2004 | Orban, III | 600/106 |
| 2004/0249367 A1 * | 12/2004 | Saadat et al. | 606/1 |
| 2004/0249395 A1 * | 12/2004 | Mikkaichi et al. | 606/144 |
| 2005/0065536 A1 * | 3/2005 | Ewers et al. | 606/153 |
| 2005/0075653 A1 * | 4/2005 | Saadat et al. | 606/139 |
| 2005/0090709 A1 * | 4/2005 | Okada et al. | 600/104 |
| 2005/0113640 A1 * | 5/2005 | Saadat et al. | 600/106 |
| 2005/0119524 A1 * | 6/2005 | Sekine et al. | 600/114 |
| 2005/0119671 A1 * | 6/2005 | Reydel et al. | 606/144 |
| 2005/0165272 A1 * | 7/2005 | Okada et al. | 600/114 |
| 2005/0203489 A1 * | 9/2005 | Saadat et al. | 606/1 |
| 2005/0245945 A1 * | 11/2005 | Ewers et al. | 606/153 |
| 2005/0250984 A1 * | 11/2005 | Lam et al. | 600/102 |
| 2005/0250985 A1 * | 11/2005 | Saadat et al. | 600/102 |
| 2005/0250986 A1 * | 11/2005 | Rothe et al. | 600/102 |
| 2005/0250987 A1 * | 11/2005 | Ewers et al. | 600/102 |
| 2005/0250988 A1 * | 11/2005 | Ewers et al. | 600/102 |
| 2005/0251157 A1 * | 11/2005 | Saadat et al. | 606/153 |
| 2005/0251160 A1 * | 11/2005 | Saadat et al. | 606/153 |
| 2005/0251161 A1 * | 11/2005 | Saadat et al. | 606/153 |
| 2005/0251162 A1 * | 11/2005 | Rothe et al. | 606/153 |
| 2005/0251165 A1 * | 11/2005 | Vaughan et al. | 606/153 |
| 2005/0251166 A1 * | 11/2005 | Vaughan et al. | 606/153 |
| 2005/0251202 A1 * | 11/2005 | Ewers et al. | 606/213 |
| 2005/0251205 A1 * | 11/2005 | Ewers et al. | 606/232 |
| 2005/0251206 A1 * | 11/2005 | Maahs et al. | 606/232 |
| 2005/0251210 A1 * | 11/2005 | Westra et al. | 606/232 |
| 2005/0267335 A1 * | 12/2005 | Okada et al. | 600/173 |
| 2006/0135849 A1 * | 6/2006 | Adams | 600/104 |
| 2006/0161185 A1 * | 7/2006 | Saadat et al. | 606/153 |
| 2006/0253128 A1 * | 11/2006 | Sekine et al. | 606/139 |
| 2006/0271073 A1 * | 11/2006 | Lam et al. | 606/148 |
| 2006/0271074 A1 * | 11/2006 | Ewers et al. | 606/148 |
| 2006/0271101 A1 * | 11/2006 | Saadat et al. | 606/205 |
| 2007/0073322 A1 * | 3/2007 | Mikkaichi et al. | 606/153 |
| 2007/0112362 A1 * | 5/2007 | Mikkaichi et al. | 606/153 |
| 2007/0135678 A1 * | 6/2007 | Suzuki | 600/37 |
| 2007/0142849 A1 * | 6/2007 | Ewers et al. | 606/153 |
| 2007/0157937 A1 * | 7/2007 | Mikkaichi et al. | 128/898 |
| 2007/0167675 A1 * | 7/2007 | Miyamoto et al. | 600/104 |
| 2007/0167676 A1 * | 7/2007 | Miyamoto et al. | 600/104 |
| 2007/0197864 A1 * | 8/2007 | Dejima et al. | 600/106 |
| 2008/0015409 A1 * | 1/2008 | Barlow et al. | 600/106 |
| 2008/0086155 A1 * | 4/2008 | Rothe et al. | 606/153 |
| 2008/0177304 A1 * | 7/2008 | Westra et al. | 606/232 |
| 2008/0200930 A1 * | 8/2008 | Saadat et al. | 606/139 |
| 2009/0018552 A1 * | 1/2009 | Lam et al. | 606/139 |
| 2009/0023985 A1 * | 1/2009 | Ewers | 600/104 |
| 2009/0023987 A1 * | 1/2009 | Okada et al. | 600/106 |
| 2009/0030272 A1 * | 1/2009 | Yamamoto et al. | 600/106 |
| 2009/0076319 A1 * | 3/2009 | Muyari | 600/106 |
| 2009/0259141 A1 * | 10/2009 | Ewers et al. | 600/562 |
| 2009/0312602 A1 * | 12/2009 | Sakamoto et al. | 600/104 |
| 2009/0326578 A1 * | 12/2009 | Ewers et al. | 606/213 |
| 2010/0010296 A1 * | 1/2010 | Piskun | 600/104 |
| 2010/0010297 A1 * | 1/2010 | Piskun | 600/104 |
| 2010/0010457 A1 * | 1/2010 | Ewers et al. | 604/272 |
| 2010/0042115 A1 * | 2/2010 | Saadat et al. | 606/142 |
| 2010/0113873 A1 * | 5/2010 | Suzuki et al. | 600/106 |
| 2010/0137681 A1 * | 6/2010 | Ewers et al. | 600/102 |
| 2010/0174140 A1 * | 7/2010 | Aznoian et al. | 600/106 |
| 2010/0174312 A1 * | 7/2010 | Maahs et al. | 606/213 |
| 2010/0191052 A1 * | 7/2010 | Surti et al. | 600/106 |
| 2010/0211086 A1 * | 8/2010 | Ewers et al. | 606/153 |
| 2010/0249500 A1 * | 9/2010 | Reydel et al. | 600/104 |
| 2010/0249814 A1 * | 9/2010 | Vaughan et al. | 606/153 |

FOREIGN PATENT DOCUMENTS

| | | | |
|---|---|---|---|
| JP | 2004-065679 | 3/2004 | |
| WO | WO 2005/058239 | 6/2005 | |
| WO | WO 2007/011039 A1 * | 1/2007 | A61B 17/28 |

OTHER PUBLICATIONS

Office Action issued by Japanese Patent Office on Dec. 4, 2012 in connection with corresponding Japanese Application 2009-158993 and English translation thereof.

* cited by examiner

ENDOSCOPIC SURGICAL OPERATION METHOD

BACKGROUND OF THE INVENTION

1. Field of the Invention

The present invention relates to an endoscopic surgical operation method for removing diseased tissue by conducting full thickness resections to the living tissue of an organ, for example, a digestive canal by using an endoscope.

2. Background Art

Conventional endoscopic mucosal resection for treating a diseased tissue, for example, cancer developed on a digestive canal without carrying out an abdominal operation has been commonly in practice in which a mucosa deteriorated by a diseased tissue is resected with an instrument attached to an endoscope inserted into a body cavity from the mouth or an anus.

In particular, en bloc resection, i.e., full thickness resection including a mucosa, a submucosa, a muscle coat, and a serosa has been considered in recent years for resecting the diseased tissue reliably and facilitating histopathological diagnosis for the resected diseased tissue.

An example of the full thickness resection conducted to a section including an diseased tissue in a hollow organ, for example, a stomach or a colon disclosed in the specification of U.S. Pat. No. 7,334,718 is a surgery method in which, a cylindrical housing is attached to the distal end of an endoscope; an internal tissue is retracted into the housing by using a grasping forceps; the internal organ is resected in the vicinity of the opening of the housing by using rotational blades; and a distal end section of the internal tissue relative to the resected point is sutured with a stapler.

Another example of a full thickness resection conducted to a section including an diseased tissue in a hollow organ disclosed in the specification of U.S. Pat. No. 7,326,221 is a surgery method in which, a cylindrical housing is attached to the distal end of an endoscope; an internal tissue is retracted into the housing by means of suctioning; the suctioned living tissue is tailored using a T-bar suture instrument; and the living tissue is resected in this state. In these cases, the scope of resection is limited since these surgery methods suctions the living tissue into the housing and then resect the living tissue, therefore, full thickness resection is difficult in the case of a widely spreading diseased tissue.

SUMMARY OF THE INVENTION

Endoscopic surgical operation method according to the present invention includes: a step of lifting a living tissue including an diseased tissue located distally relative to an operation channel of an endoscope inserted through a natural orifice; a step of suturing overlapping sections of the living tissue positioned basal relative to the diseased tissue lifted by a suturing means projecting distally from the operation channel of the endoscope after the lifting step; and a step of resecting the living tissue between the sutured regions and the diseased tissue endoscopically after suturing the overlapping sections of the living tissue in plural points that surround the diseased tissue by repeating the lifting step and the suturing step.

PREFERRED EMBODIMENTS

Figure 1:
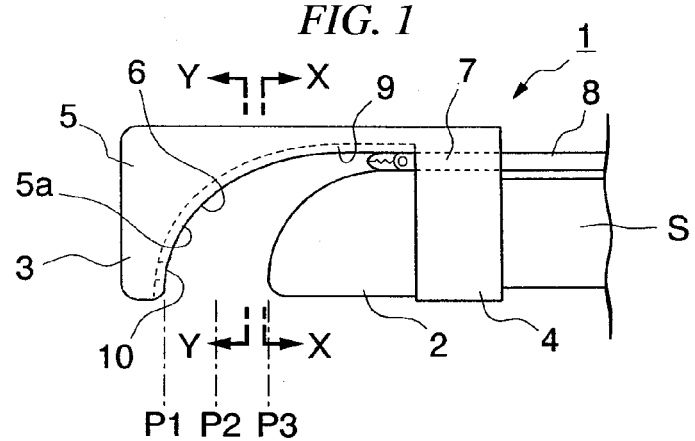
FIG. 1 is a side view of the distal end section of a device for conducting the endoscopic surgical operation method of the present invention.
Figure 2:
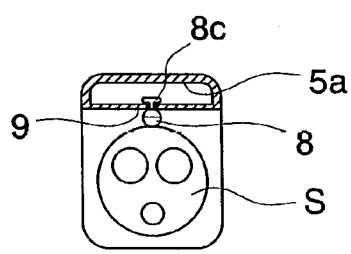
FIG. 2 is a cross sectional view of the aforementioned device taken along the line X-X.
Figure 3:
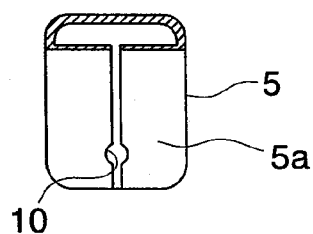
FIG. 3 is a cross sectional view of the aforementioned device taken along the line Y-Y.

Embodiments of the present invention will be explained. A device used for the surgery method will be explained prior to explanation of the endoscopic surgical operation method of the present invention. FIG. 1 is a side view showing a device 1 attached to the distal end of an endoscope S. FIG. 2 is a cross-sectional view taken along the line X-X in FIG. 1, and FIG. 3 is a cross-sectional view taken along the line Y-Y in FIG. 1.

The device 1 includes: a cap 2 fitting onto the distal end of the endoscope S; and a slide block 3 attached to the distal end of the endoscope S and being capable of moving in the axial line direction of the endoscope S. The cap 2 is formed to have a ring shape. In addition, the cap 2 is made of a transparent material in an attempt not to disturb visual field of the endoscope S, and the lower end of the cap 2 projects distally and has an arch shape in side view. The slide block 3 includes: a freely movable proximal end section 4 fitting onto the distal end of the endoscope S; and a forward expansion section 5 expanding distally from the upper end of the proximal end section 4. The slide block 3 is also made of a transparent material in an attempt not to disturb the visual field of the endoscope S. In addition, the position of the slide block 3 relative to the endoscope S is changed with an operation wire, not shown in the drawings, to one of positions including: a position P1 distal relative to the endoscope S; a position P2 slightly proximal from there; and a position P3 between the two positions P1 and P2. In addition, it is preferable that the operation wire has a latchet mechanism that can hold the slide block 3 at an arbitrary position. In addition, a space formed between the forward expansion section 5 of the slide block 3 and the cap 2 is a living-tissue-introducing section 6. An instrument holder 7 is provided in an upper section of the proximal end section 4. A so-called externally-installable lift instrument 8 is inserted through the instrument holder 7. The lift instrument 8 is capable of moving along the axial line so that the lift instrument 8 passes in the exterior of an endoscope S but not inserted through the channel of the endoscope S. An example of the lift instrument 8 shown here is a grasping forceps.

Figure 4:
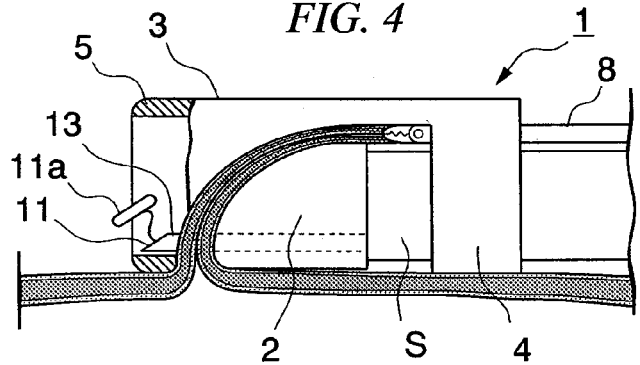
FIG. 4 is a side view of the distal end section of the aforementioned device in use.

As shown in FIG. 2, the hollow forward expansion section 5 has a rectangular cross section having a bottom surface section 5a formed in the lower part thereof and having an arch concave shape banding along the outer shape of the cap 2. A guide section 9 which is a guide groove or a guide rail is provided on the bottom surface of the bottom surface section 5a. A mating guide section 8c attached to the distal end of the instrument 8 engages with the guide section 9. The instrument 8 being extended or retracted is guided along the guide section 9. In addition, a through-hole 10 is formed on the bottom surface section 5a. The distal end of a T-bar suture instrument 11 inserted through a channel of the endoscope S can penetrate the through-hole 10 as shown in FIG. 4.

The endoscopic surgical operation method using the device 1 will be explained next.

<Insertion of Endoscope into Lumen>

Figure 5:
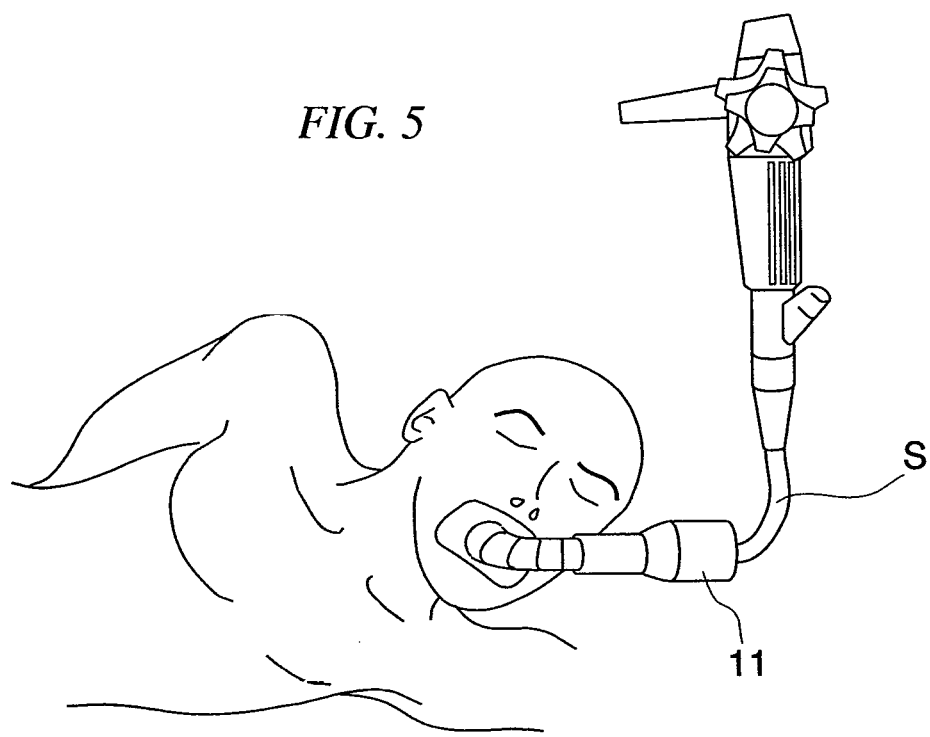
FIGS. 5 and 6 are isometric views for explaining a process of the endoscopic surgical operation method of the present invention.

As shown in FIG. 5, an insertion section of the endoscope S is inserted from a natural orifice, for example, a mouth into a lumen, for example, a stomach; the stomach or the like. is insufflated so that the lumen is in an inflated state; and then, the distal end of the endoscope S is approached to the vicinity of the object site, that is, the diseased tissue X. It should be noted that a natural orifice subject to the insertion of the endoscope S is not necessarily the mouth. The nasal cavity or anus may be used alternatively. In another configuration, the endoscope S may be inserted directly from a natural orifice into the lumen without using an overtuve 200 in contrast to an example shown in the drawing using the overtube 200 for inserting the endoscope S as shown in the drawings.

<Clarification for Diseased Tissue>

Figure 6:
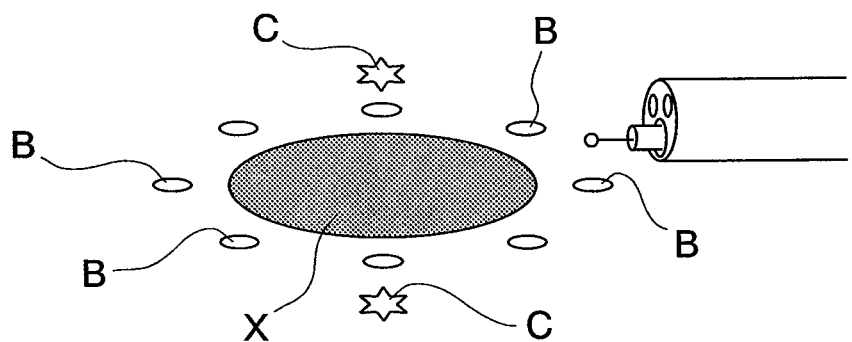

The diseased tissue X is specified based on an image obtained with an observation section provided to the distal end of the endoscope S. As shown in FIG. 6, upon specifying the diseased tissue X, markings are provided to clarify the position of the diseased tissue X. Adoptable examples of providing markings are spraying a colorant, providing markings around the diseased tissue X with a high-frequency device, and attaching marking members such as clips.

In a case of spreading a colorant, the distal end of a tube is located in the vicinity of the diseased tissue X by using, for example, an operation channel of the endoscope S, and a colorant harmless to the human body, for example, methylene blue, indigo carmine, or triazine blue is spread from the opening of the distal end. Alternatively, iodine may be sprayed in place of spreading a colorant. In the case of providing markings around the diseased tissue X with a marking device, for example, a high-frequency device, the distal end of the marking device is located in the vicinity of the diseased tissue X by using the operation channel of the endoscope S, and markings are provided to predetermined positions while observing the positions with the observation section of the endoscope S (reference symbol B in FIG. 6 indicates a section where a marking is provided). A usable marking device is a heating element such as a high-frequency knife, a high-frequency forceps, a high-frequency snare, and a heat probe, or an ultrasonic device. In the case of attaching marking members such as clips or the like, the distal end of a clip-retaining device is located in the vicinity of the diseased tissue X by using the operation channel of the endoscope S, and clips are attached to predetermined positions around the diseased tissue X while observing the positions with the observation section of the endoscope S.

<Lifting of Living Tissue>

Subsequently, the living tissue in the vicinity of the diseased tissue X is lifted by using the device 1 shown in the previously explained FIGS. 1 to 4. The device 1 may be installed to the endoscope S initially so that the device 1 is inserted into the body cavity together with the endoscope S unitarily. Alternatively the endoscope including a marking instrument upon conducting the observation and providing markings may be retracted from the overtube 11 temporarily, and the endoscope having the initially-installed device 1 may be inserted into the lumen.

Markings are provided around the site which is subject to be lifted before lifting the living tissue (see reference symbol C in FIG. 6). The points having the markings are lifted, and the diseased tissue itself is not grasped directly and lifted. As previously explained, an example of providing markings is to provide markings onto the living tissue with a high-frequency device or the like or to attach marking members such as clips. The markings may be provided simultaneously or separately with respect to the markings provided for clarifying the position of the diseased tissue X.

Figure 7:
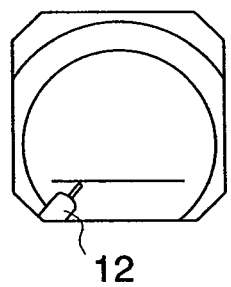
FIG. 7 shows an image obtained through the endoscope for explaining a process of the endoscopic surgical operation method according to an embodiment of the present invention.
Figure 8:
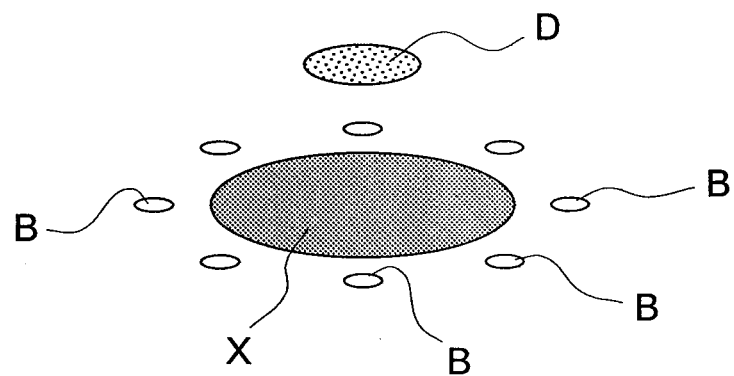
FIG. 8 is an isometric view for explaining a process of the endoscopic surgical operation method according to an embodiment of the present invention.

Also, as shown in FIG. 7, the mucosa corresponding to the site C is removed or incised with a device 12 for incision use, and a muscle coat D thereinside is exposed in advance (see FIG. 8). The muscle coat D is thus exposed prior to lift because it is difficult to lift a full thickness of site including a mucosa, a submucosa, a muscle coat, and a serosa when a grasping forceps grasps a mucosa. A device for incision use to expose the muscle coat D is a heating element such as a high-frequency knife, a high-frequency forceps, a high-frequency snare, and a heat probe, or an ultrasonic device. Alternatively, a scissors forceps or the like may be used.

Figure 9:
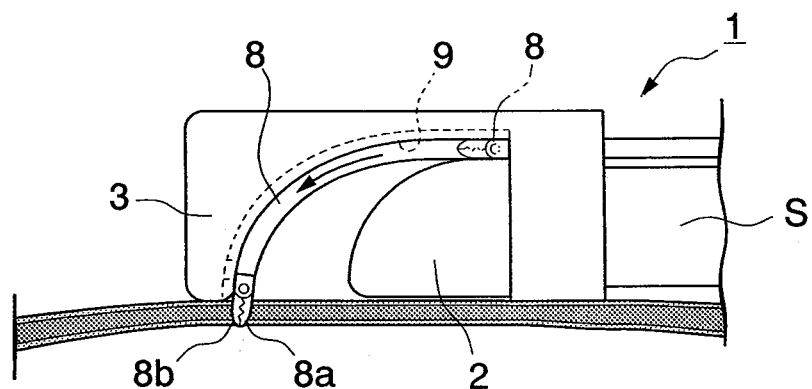
FIG. 9 is a side view for explaining a process of the endoscopic surgical operation method according to an embodiment of the present invention.
Figure 10:
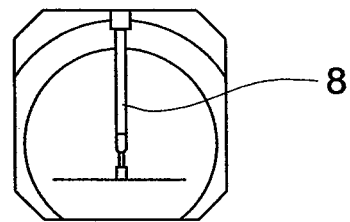
FIG. 10 shows an image obtained through the endoscope for explaining a process of the endoscopic surgical operation method according to an embodiment of the present invention.
Figure 11:
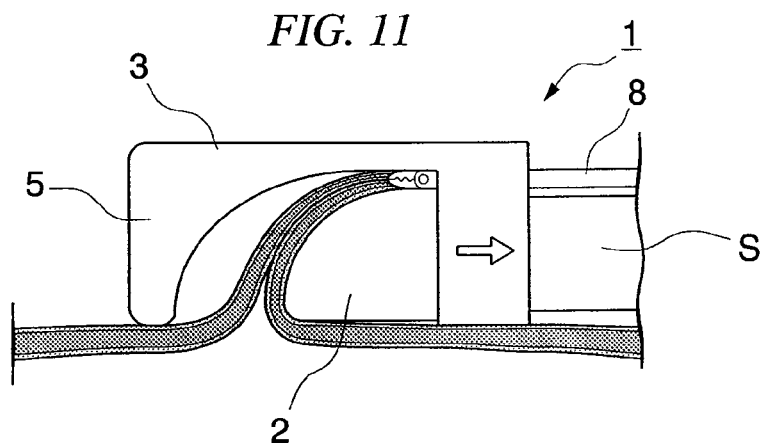
FIGS. 11 and 12 are side views for explaining a process of the endoscopic surgical operation method according to an embodiment of the present invention.

Subsequently, the lift instrument 8 of the device 1 is positioned above a site subject to lift in which the muscle coat D is exposed. Subsequently, the lower part of the cap 2 of the device 1 and the lower part of the slide block 3 are directed toward the living tissue respectively and compressed downward as shown in FIG. 9. The lift instrument 8 is extended in this state. The lift instrument 8 extends along the guide section 9 provided on the bottom surface of a bottom section 5a of the forward expansion section 5 and is finally disposed to be opposed to the muscle coat D in the site subject to lift. Subsequently, a pair of jaw sections 8a and 8b are opened by a proximal operation of an instrument and compressed downward in this state, and then the jaw sections 8a and 8b are closed (see FIG. 11). That is, the muscle coat or a living tissue disposed therebeneath is grasped with the pair of jaw sections 8a and 8b. It should be noted that the incision of mucosa may be omitted based on the length of organ or a configuration associated with a grasping instrument.

Subsequently, the air in the lumen, a stomach or the like. is purged to provide slack to the lumen. Slack is provided to the lumen in this manner for facilitating a lifting of the living tissue. The air purged from the lumen is in a degree that does not disturb the observation with the endoscope and the lifting operation The lift instrument 8 is drawn proximally upon providing slack to the lumen while the muscle coat D is grasped with the pair of jaw sections 8a and 8b. The a pair of jaw sections 8a and 8b are retracted while grasping the muscle coat D or the like and being guided along the guide section 9. That is, in the beginning, the a pair of jaw sections 8a and 8b are lifted substantially orthogonally with respect to the surface of the living tissue, and then the pair of jaw sections 8a and 8b are moved proximally relative to the endoscope S so that the pair of jaw sections 8a and 8b are substantially parallel to the surface of the living tissue. The living tissue in a folding state drawn by moving the pair of jaw sections 8a and 8b is retracted into the living-tissue-introducing section 6.

Figure 12:
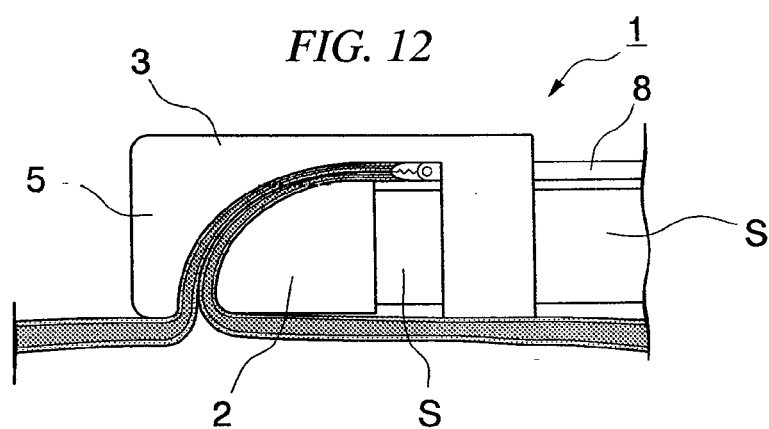

Subsequently, as shown in FIG. 12, the forward expansion section 5 is drawn proximally to the endoscope S by operating an operation wire, not shown in the drawing. This results in shortening the distance between the forward expansion section 5 and the cap 2, thereby allowing a distally-located living tissue in a lifted state to make close contact with a proximally-located living tissue in a lifted state.

That is, the device 1 has two functions including: a function of compressing the living tissue downward with the lower part of the forward expansion section 5 and the lower part of the cap 2 so that a wide range of the living tissue subject to lift is not raised unitarily; and a function of drawing the distally-located living tissue proximally and overlaying the distally-located living tissue with the proximally-located living tissue making close contact therewith so that a suture operation, which will be explained later, can be facilitated after the lifting operation.

<Suturing Living Tissue>

Subsequently, a suturing means is inserted into the lumen, and the serosas of the living tissue lifted with the inserted suturing means are contacted closely and fixed.

Figure 13:
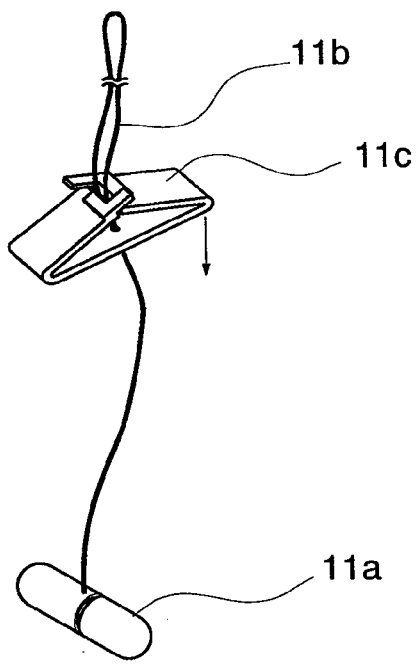
FIG. 13 is an isometric view showing an example of a suture instrument used in the endoscopic surgical operation method according to an embodiment of the present invention.

In the case of using, for example, the T-bar suture instrument 11 as the suturing means, the T-bar suture instrument 11 having the T-bar 11a pre-installed as shown in FIG. 13 is disposed to be opposed to the lifted living tissue by using the operation channel of the endoscope S. In addition, as shown in FIG. 4, a puncture needle 13 is extended to penetrate the distally-located living tissue, the proximally-located living tissue, and the through-hole 10 of the bottom section 5a. Subsequently, the T-bar 11a is extended from the distal end of the puncture needle 13 and retained. After that, the puncture needle 13 is removed from the living tissue, and the distally-located living tissue and the proximally-located living tissue are placed between a fastener 11c and the T-bar 11a and fixed there by pulling a thread 11b. It is preferable that the endoscope S in this state be directed upward. This is to prevent the puncture needle 13 from damaging ambient organs when the puncture needle 13 is projected from the operation channel of the endoscope S. Alternatively, damage to ambient organs can be prevented in another configuration capable of limiting a projection degree of the puncture needle 13 with a stopper or the like, not shown in the drawing, for preventing the puncture needle 13 from projecting from the distal end of the forward expansion section 5.

The suturing means in place of the T-bar suture instrument 11 is a stapler, a thread, a clip, a resilient coil or the like.

After that, plural basal points of the living tissues in overlapping state including the diseased tissue X are sutured by repeating the aforementioned lift and suture of the living tissue.

Figure 14A:
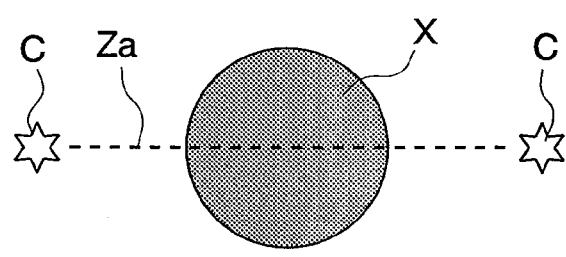
FIGS. 14A and 15A are plan views for explaining a process of the endoscopic surgical operation method according to an embodiment of the present invention.
Figure 14B:
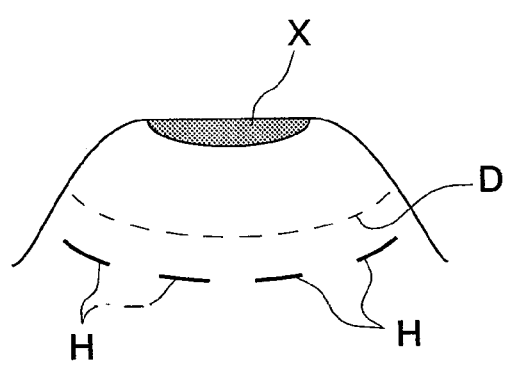
FIGS. 14B and 15B are isometric views for explaining a process of the endoscopic surgical operation method according to an embodiment of the present invention.

The living tissues including the diseased tissue X are overlayed in two forms: in one form, the living tissues are bent along a line Za trespassing the diseased tissue X as shown in FIGS. 14A and 14B; and in another form, the living tissues are bent along a line Zb not trespassing the diseased tissue X so that the diseased tissue X comes to one side with respect to the line Zb.

Figure 15A:
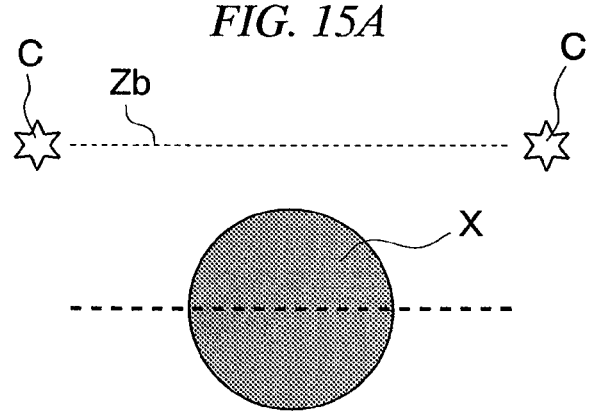
Figure 15B:
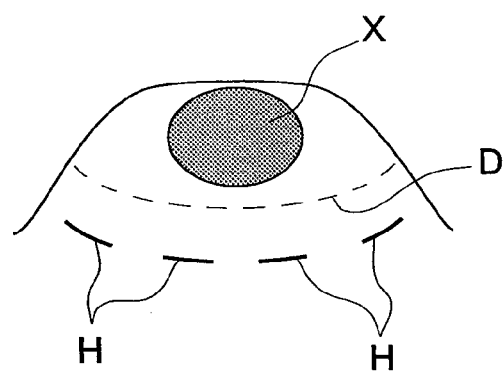

In either case, the two pieces of living tissue including the diseased tissue X in an overlaid state are sutured at plural lifted basal points. Reference symbols H indicate the sutured points as shown in FIGS. 14B and 15B. As shown in FIG. 4, accretion of the closely-contacting serosas occurring over time in the sutured points results in joining the two pieces of living tissue unitarily.

<En Bloc Resection of Diseased Tissue in Full Thickness>

Upon concluding a sequence of operations associated with lift and suture, the lumen, a stomach or the like is insufflated to obtain a visual field for the endoscope S.

Figure 16:
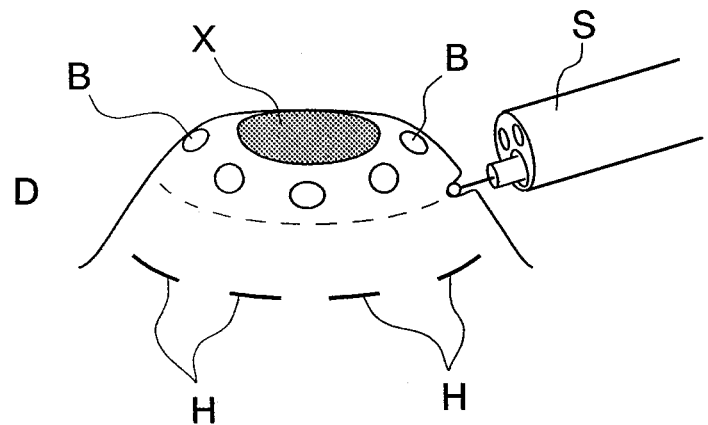
FIGS. 16 and 17 are isometric views for explaining a process of the endoscopic surgical operation method according to an embodiment of the present invention.

The diseased tissue X is resected from the fixed living tissue by resecting the full thickness of tissues between the diseased tissue X and the sutured sections. Reference symbol D indicates the point subject to resection as shown in FIGS. 14B, 15B, and 16. The device which is inserted into the operation channel of the endoscope S for resecting the living tissue in this case is a high-frequency device such as a high-frequency knife, a high-frequency forceps, and a high-frequency snare or the like, or an ultrasonic device. In addition, a scissors forceps may be used for incision. Alternatively, a stapler may be used for incision. Alternatively, the living tissue grasped and lifted at predetermined points may be resected while applying tension thereto with a grasping forceps in an attempt to keep trapping the living tissue.

The aforementioned resection method can prevent contamination in the abdominal cavity because the section subject to resection is sutured in advance, and gastric contents or air is prevented from leaking from the resected sections into the abdominal cavity. In addition, the configuration in which the lifting and the suturing of the tissue are repeated, and the diseased tissue is surrounded by the sutured section instead of retracting the living tissue into a limited housing space or the like and resecting the tissue does not limit the ranges of the suturing points and subsequently-resecting points, thereby allowing a large area of full thickness resection. In addition, resected ends may be further closed with clips or the like for obtaining more reliable sealing capability at the resected sections.

<Hemostasis in Bleeding Site>

In addition, in a case of observing a bleeding from the resected site when dissection is conducted, hemostatic treatment is conducted by using, for example, a high-frequency device such as a high-frequency knife, a high-frequency forceps, and a high-frequency snare or the like or a heating element such as a heat probe or the like. Alternatively, astriction may be conducted by retaining clips, snares, or rubber members or the like. In addition, chemical hemostatic treatment may be conducted by, for example, injecting or spreading chemicals.

Subsequently, a leak test as to whether the resected section is fully closed may be conducted by, for example, insufflating the lumen and examining the change in pressure after a predetermined time. Granted that leak is detected, the opening section may be sutured more densely by the aforementioned suturing means.

In addition, the resected section may be closed with a device such as a clip, a snare, or a rubber member for preventing the resected section from reopening after the surgery.

<Collection of Diseased tissue>

Figure 17:
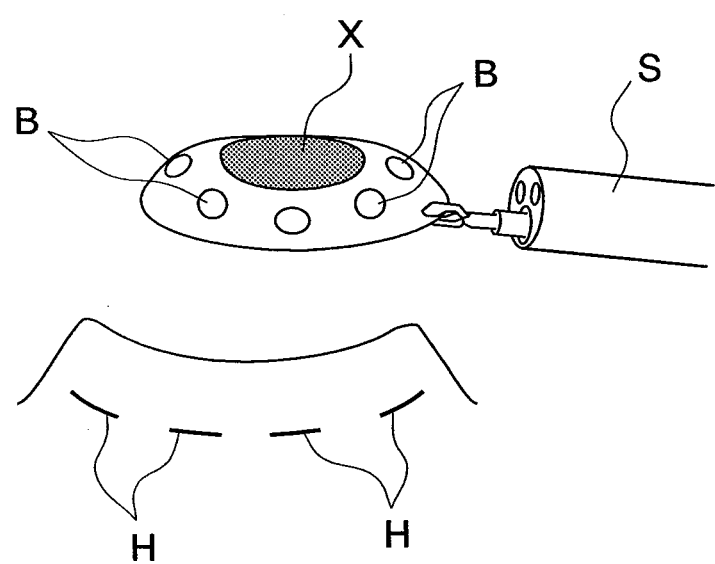
Figure 18:
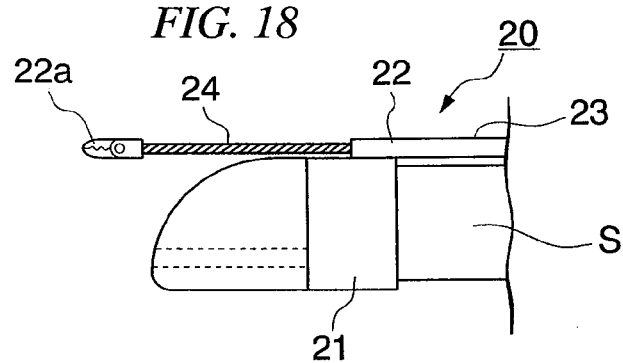
FIGS. 18 to 21 are side views showing a modified example of the device for carrying out the endoscopic surgical operation method of the present invention.
Figure 19:
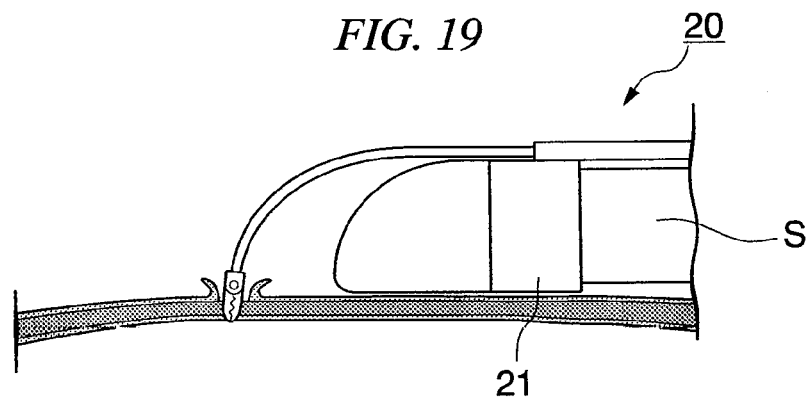
Figure 20:
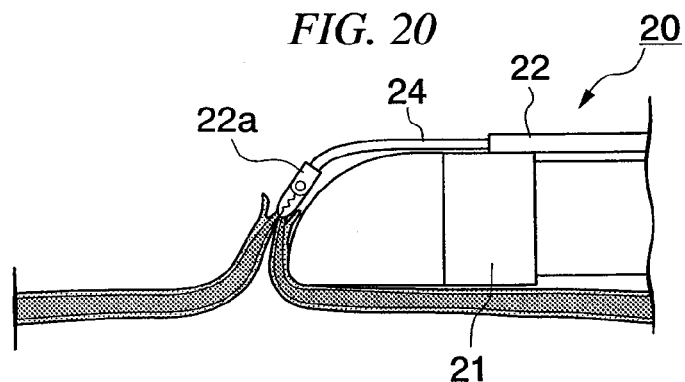
Figure 21:
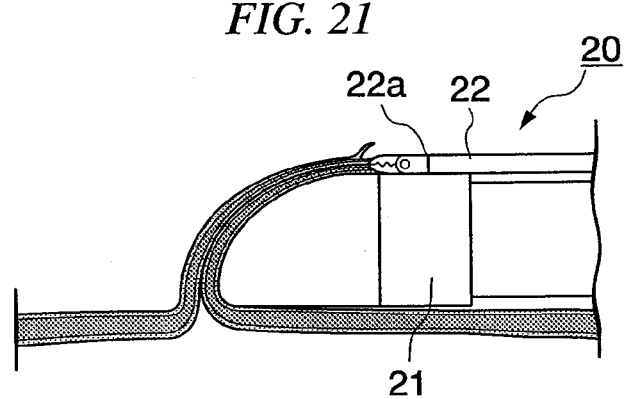

After the resection in the aforementioned manner, the resected living tissue including the diseased tissue is collected with an instrument for collection use as shown in FIG. 17. A usable instrument for collection use is a grasping forceps, a tripod forceps, a basket forceps, or a snare or the like. Alternatively, the diseased tissue may be collected by means of suctioning using a channel of an endoscope for suction use or a tube such as an overtube or the like. Further alternatively, the diseased tissue may be collected with a net member such as a tissue-collection net.

MODIFIED EXAMPLE 1

It should be noted that, in the following modified examples, structural elements that are equivalent to those of the aforementioned embodiment will be assigned the same numeric symbols and redundant explanations thereof will be omitted.

FIGS. 18 to 21 show a modified example of the device for endoscopically lifting the living tissue in the vicinity of the diseased tissue X. A device 20 shown here has a cap 21 attached to the endoscope S, and has a lift instrument 22 of externally-attachable type disposed along the axial line and being capable of moving therealong. The lift instrument 22 has an outer tube 23 having a coil sheath 24 inserted therethrough and being capable of extending or retracting. A treatment section 22a is attached to the distal end of the coil sheath 24.

The coil sheath 24 has a pre-curve. When the distal end of the coil sheath 24 is projected from the outer tube 23 by a predetermined length or longer, the treatment section 22a of the distal end is substantially orthogonal to and opposed against the living tissue disposed therebeneath. In this case, since the muscle coat that has been subjected to removal of mucosa in advance and exposed externally can be grasped with the treatment section 22a, the living tissue including the diseased tissue can be lifted by drawing the muscle coat in this state together with the coil sheath 24 proximally relative to the endoscope S.

Figure 22A:
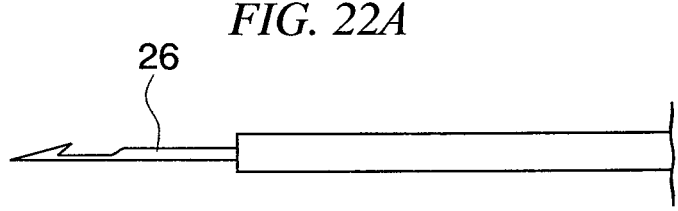
FIGS. 22A to 22D are side views showing an example of a grasping instrument used for carrying out the endoscopic surgical operation method of the present invention.
Figure 22B:
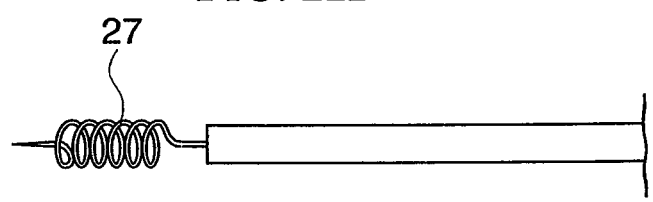
Figure 22C:
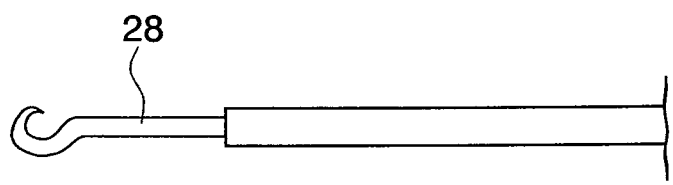
Figure 22D:
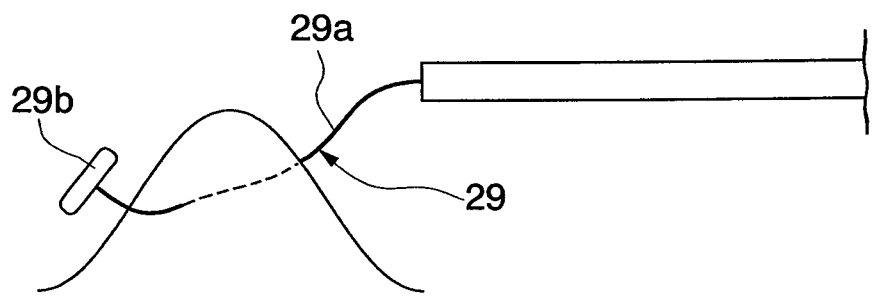

It should be noted that, an instrument for lifting and grasping the living tissue is a forceps 26 having an arrowhead shape as shown in FIG. 22A, a forceps 27 having a spiraL-letter shape as shown in FIG. 22B, a forceps 28 having a distal end having a bending hook shape as shown in FIG. 22C, or an anchor 29 having a T-bar 29b attached to the distal end of a thread 29a as shown in FIG. 22D.

MODIFIED EXAMPLE 2

Figure 23:
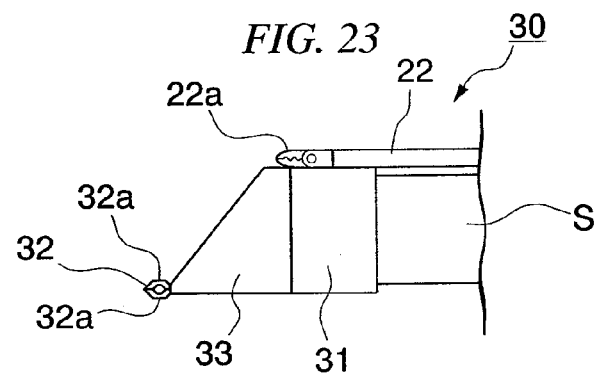
FIGS. 23 to 25B are side views showing another modified example of the device for carrying out the endoscopic surgical operation method of the present invention.
Figure 24:
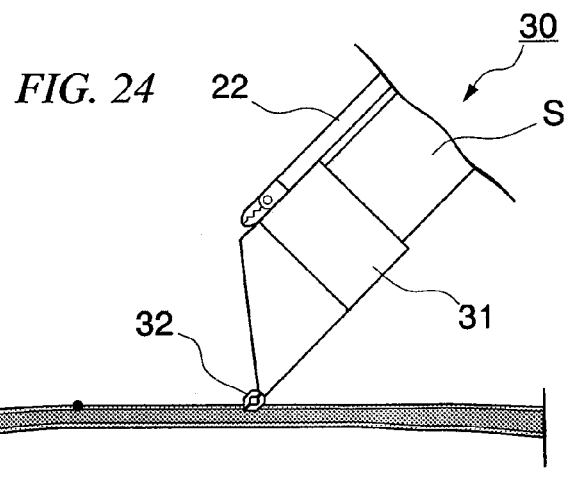

FIGS. 23 to 25 show another modified example of the device for endoscopically lifting the living tissue in the vicinity of the diseased tissue X. A device 30 in the modified example 2 is different from that shown in the aforementioned modified example 1 because of having a grasping mechanism 32 provided at a lower section of the distal end of a cap 31 attached to the distal end of the endoscope S. That is, a pair of jaw sections 32a and 32a attached to the distal end of the cap 31 and are capable of grasping a living tissue are opened or closed by an extending or a retracting operation to an operation wire, not shown in the drawing, extending proximally through, for example, the channel of an endoscope. In addition, a cap tip end section 33 is capable of moving in the axial line direction relative to a cap main body. The position of the cap tip end section 33 relative to the cap main body is determined by operating an operation section such as a wire or the like which is not shown in the drawing.

The device 30, upon determining the site of the living tissue subject to being lifted, grasps the living tissue with the pair of jaw sections 32a and 32a attached to the distal end of the cap 31 and sets the position of the distal end of the endoscope S. Simultaneously, the angle of the distal end of the endoscope S with respect to the living tissue is set as shown in FIG. 24, and after that, the externally-attachable lift instrument 22 is extended. Subsequently, the muscle coat having previously undergone removal of mucosa from the surface thereof to be exposed externally is grasped with the treatment section 22a of the distal end.

Figure 25A:
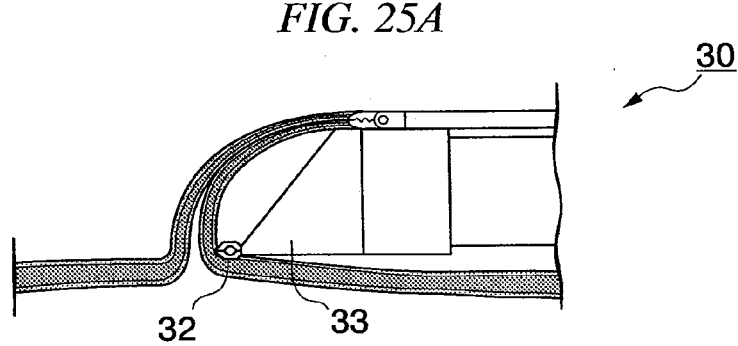
Figure 25B:
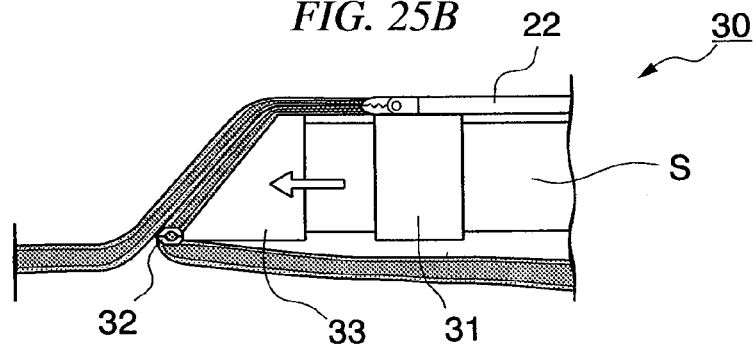

After that, the attitude of the endoscope S is adjusted so that the endoscope S is in parallel with the surface of the living tissue as shown in FIG. 25A, and the grasped living tissue can be lifted by drawing the grasped living tissue proximally together with the coil sheath 24. In addition, the cap tip end section 33 is operated and extended if necessary as shown in FIG. 25B. This results in causing the distally-located living tissue to make close contact with the proximally-located living tissue. Therefore, the following suturing process is facilitated.

It should be noted that accurate resection can be ensured by the device 30 in this case capable of determining the positional relationship between the suturing section and the grasping section strictly by grasping the living tissue with the grasping mechanism 32 attached to the distal end of the cap 31. In addition, a lifting instrument usable in this case may not have a pre-curve.

MODIFIED EXAMPLE 3

Figure 26:
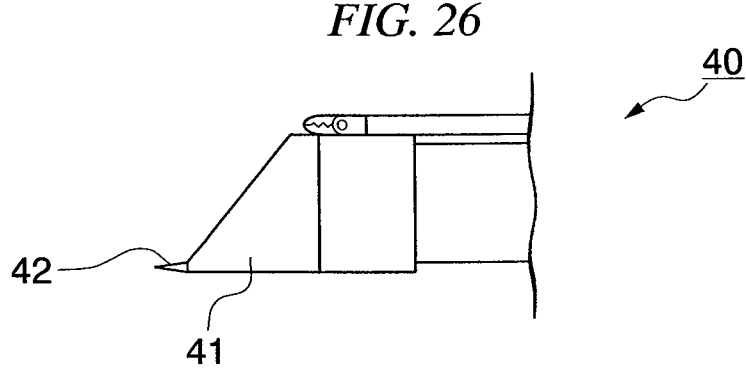
FIG. 26 is a side view showing another modified example of the device for carrying out the endoscopic surgical operation method of the present invention.

FIG. 26 shows another modified example of the device for endoscopically lifting the living tissue in the vicinity of the diseased tissue X. A device 40 shown in FIG. 26 has a cap 41 having a needle 42 attached to the distal end thereof According to the device 40, the position of the cap 41 relative to the living tissue and the position of the distal end of the endoscope S having the cap 41 attached thereto relative to the living tissue can be determined by inserting the needle 42 of the distal end of the cap 41 into the living tissue.

MODIFIED EXAMPLE 4

Figure 27:
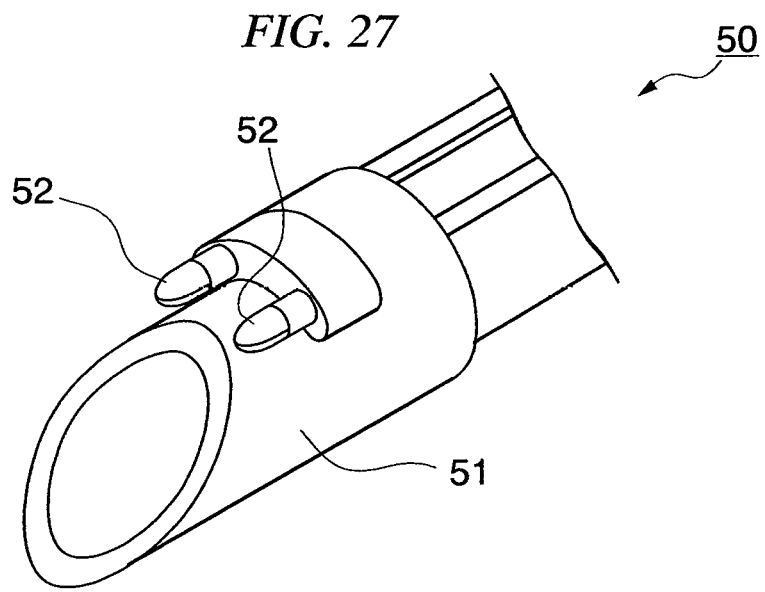
FIGS. 27 and 28 are isometric views showing another modified example of the device for carrying out the endoscopic surgical operation method of the present invention.
Figure 28:
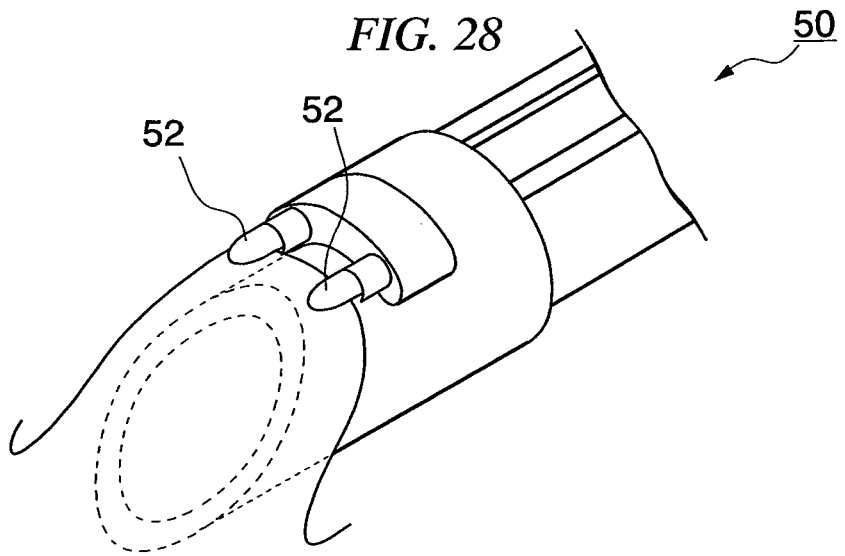

FIGS. 27 and 28 show another modified example of the device for endoscopically lifting the living tissue in the vicinity of the diseased tissue X. A device 50 shown here has two externally-attachable and freely-extendable-and-retractable lift instruments 52 attached above a cap 51 and aligned laterally while placing the cap 51 therebetween. It should be noted that the present invention is not limited to the configuration attaching two pieces of lift instruments 52; that is, three or more pieces of the lift instruments 52 may be attached; and alternatively, one piece of the lift instrument 52 may be attached as long as the width of the treatment section thereof is designed to be several times as wide as that of an ordinary treatment instrument.

The living tissue lifted by using the device 50 having the aforementioned configuration and sutured by projecting the suture means from the operation channel of the endoscope S is further compressed by the lower end of the cap 51 and grasped with the laterally-aligned lift instruments 52; therefore, the living tissue is supported at three points and lifted. Therefore, the surface of the living tissue subject to suture can be defined accurately in a suturing process.

MODIFIED EXAMPLE 5

Figure 29:
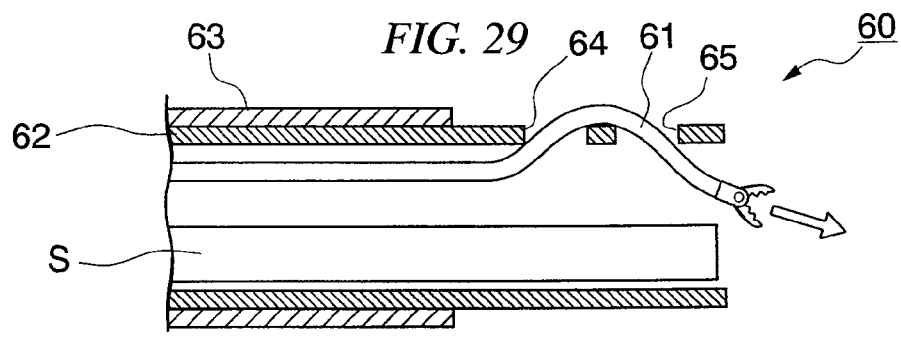
FIGS. 29 and 30 are cross-sectional views showing another modified example of the device for carrying out the endoscopic surgical operation method of the present invention.
Figure 30:
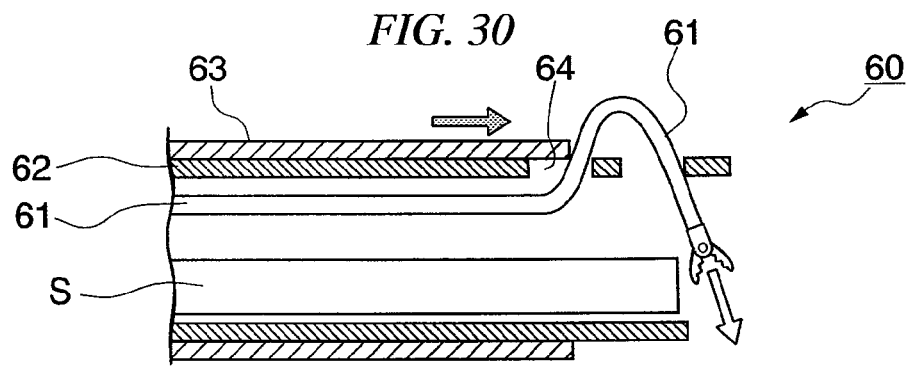

FIGS. 29 and 30 show another modified example of the device for endoscopically lifting the living tissue in the vicinity of the diseased tissue X. A device 60 shown here is provided with: an externally-attachable lift instrument 61; a first overtube 62 for accommodating the endoscope S; and a second overtube 63 disposed in the exterior of the first overtube 62 and being capable of moving along the axial line. Two holes 64 and 65 aligned in the axial line direction are formed on the distal end of the first overtube 62. The lift instrument 61 penetrates the proximally-located hole 64 from the inside and penetrates the distally-located hole 65 from the outside. In addition, the distal end of the lift instrument 61 projects outward from the opening of the distal end of the first overtube 62. The second overtube 63 in a normal state is retracted relative to the distal end so that the distal end of the second overtube 63 does not overlap the holes 64 and 65 of the first overtube 62. In the case of grasping the living tissue with the lift instrument 61, the second overtube 63 is extended as shown in FIG. 30, and the lift instrument 61 penetrating the proximally-disposed hole 64 and projecting outward is compressed by the distal end of the second overtube 63 from the proximal end to the distal end in the axial direction. The curvatures of the sections of the lift instrument 61 compressed by the second overtube 63 penetrating the holes 64 and 65 increase respectively, and the inclination angle increases in some degree relative to the living tissue therebeneath. Subsequently, it is possible to grasp the living tissue easily by extending the lift instrument 61 which maintains this state, that is, while a certain degree of significant inclination angle is maintained relative to the living tissue.

MODIFIED EXAMPLE 6

Figure 31:
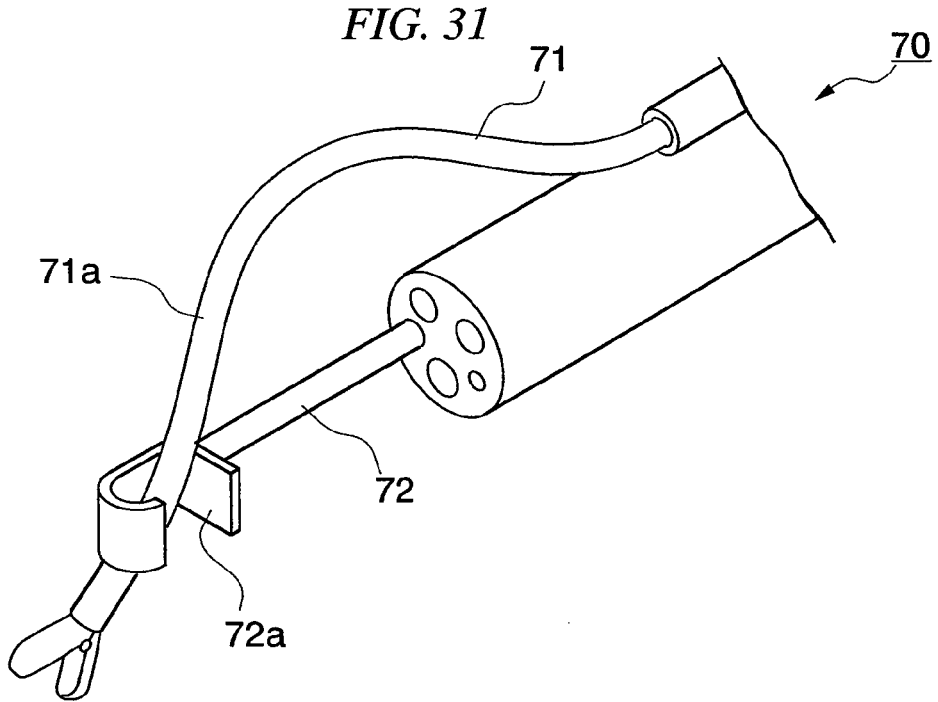
FIG. 31 is an isometric view showing another modified example of the device for carrying out the endoscopic surgical operation method of the present invention.

FIG. 31 shows another modified example of the device for endoscopically lifting the living tissue in the vicinity of the diseased tissue X. A device 70 shown here has: an externally-attachable lift instrument 71; and a tube-lock instrument 72 passing through the operation channel of the endoscope S and projecting distally. The tube-lock instrument 72 is capable of extending or retracting and locks an outer tube 71a of the instrument 71.

The device 70 can adjust the angle of the distal end of the instrument 71 with respect to the living tissue since the outer tube 71a of an instrument is locked with a locking section 72a of the distal end of the tube-lock instrument 72, and the tube-lock instrument 72 is operated to extend or retract via the operation channel. Accordingly, the living tissue can be grasped with the instrument 71 easily by setting the angle of the distal end of the instrument 71 with respect to the living tissue corresponding to the condition of the living tissue.

MODIFIED EXAMPLE 7

Figure 32:
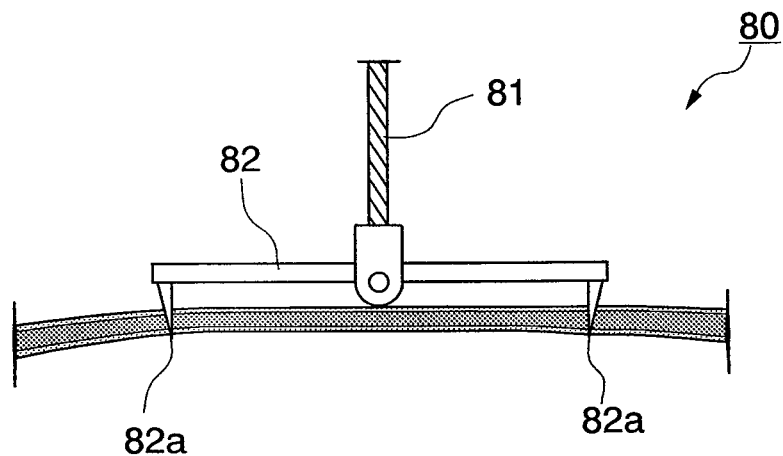
FIGS. 32 and 33 are cross-sectional views showing another modified example of the device for carrying out the endoscopic surgical operation method of the present invention.
Figure 33:
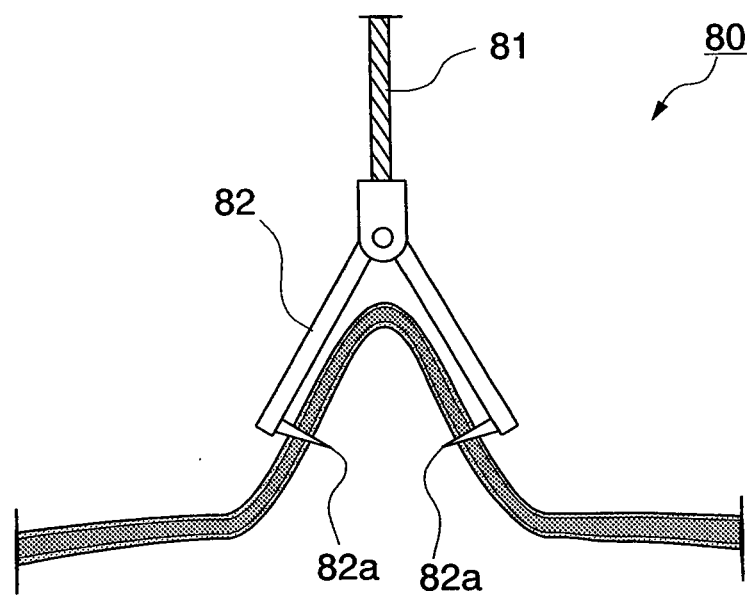
Figure 34:
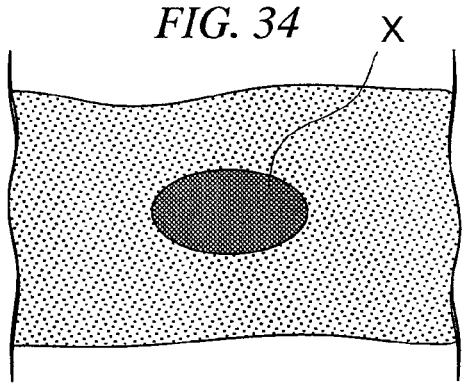
FIGS. 34 to 37 show another example of the endoscopic surgical operation method of the present invention.
Figure 35:
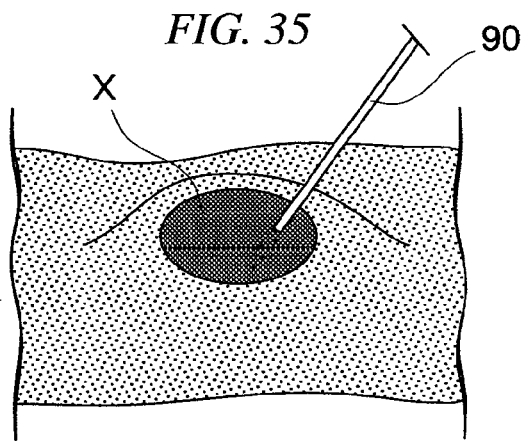
Figure 36:
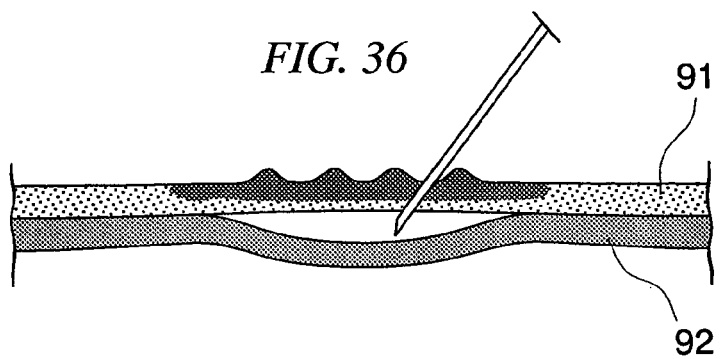
Figure 37:
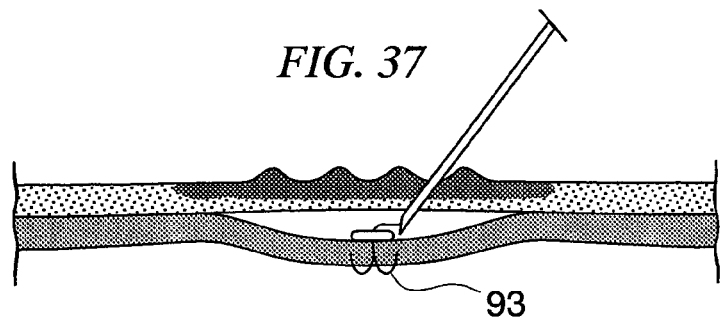

FIGS. 32 and 33 show another modified example of the device for endoscopically lifting the living tissue in the vicinity of the diseased tissue X. A device 80 shown here has a forceps 82 having needles which are attached to the distal end of a coil sheath 81. The forceps 82 having needles 82a at the distal ends thereof can be opened by an opening angle of substantially 180 degrees with an operation wire which is not shown in the drawing. The length of each needle is set to be more significant than the thickness of the mucosa of the living tissue not to project on the opposite side.

According to the device 80, the needles 82a penetrate the living tissue since the forceps 82 having the needles 82a in substantially 180 degree of opened state are disposed to be opposed to the living tissue subject to lift and extended. The needles 82a penetrate the mucosa of the living tissue and are inserted into the muscle coat. The full thickness of the living tissues can be grasped reliably without resecting the mucosa since the muscle coat can be grasped with the needles. An operation to retract the coil sheath 81 subsequently by operating the wire not shown in the drawing causes the forceps 82 having the needles to be closed, thereby allowing to grasp the living tissue. Subsequently, the living tissue in the grasped state can be lifted by drawing the forceps 82 having the needles proximally.

MODIFIED EXAMPLE 8

FIGS. 34 to 37 show another modified example of the device for endoscopically lifting the living tissue in the vicinity of the diseased tissue X. In the beginning of maneuver as shown in the drawings, an injection needle 90 is passed through the operation channel of the endoscope; the injection needle 90 is inserted into a submucosa 91 in the vicinity of the diseased tissue X; normal saline solution is injected into the submucosa 91; and then, a muscle coat 92 is removed from the submucosa 91. It should be noted that the present invention is not limited to this case in which the muscle coat 92 is removed from the submucosa 91 by means of injection using the injection needle 90. The muscle coat 92 may be removed from the submucosa 91 by using another means, for example, an insufflation balloon.

Subsequently, a guidewire is passed through the injection needle 90, and the distal end of the guidewire is retained in the muscle coat 92 which is subject to being lifted and is isolated from the submucosa 91 in advance. A hook 93 or a grasping forceps guided with the retained guidewire is fed into the muscle coat 92 and held there. Accordingly, the muscle coat in an arbitrary site of the living tissue can be lifted reliably with the locked hook 93 or the grasping forceps.

MODIFIED EXAMPLE 9

Figure 38:
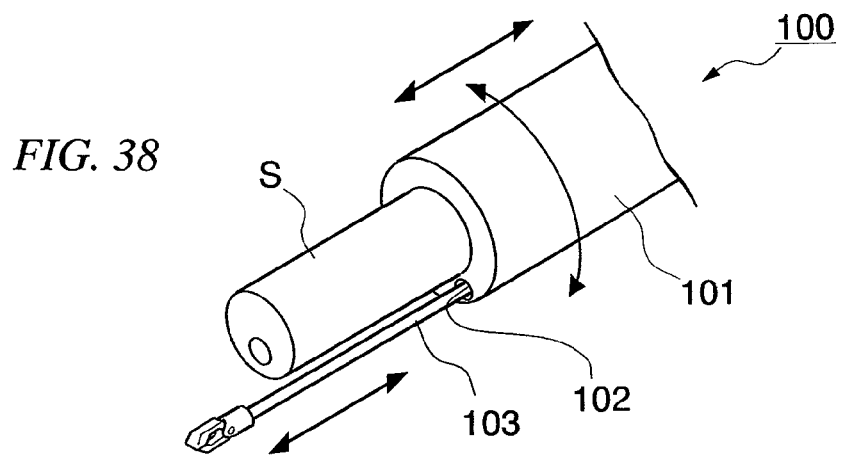
FIGS. 38 to 39C show another modified example of the device for carrying out the endoscopic surgical operation method of the present invention.
Figure 39A:
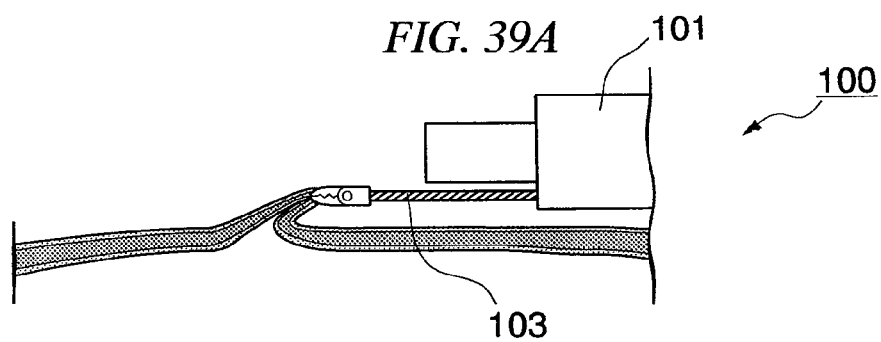
Figure 39B:
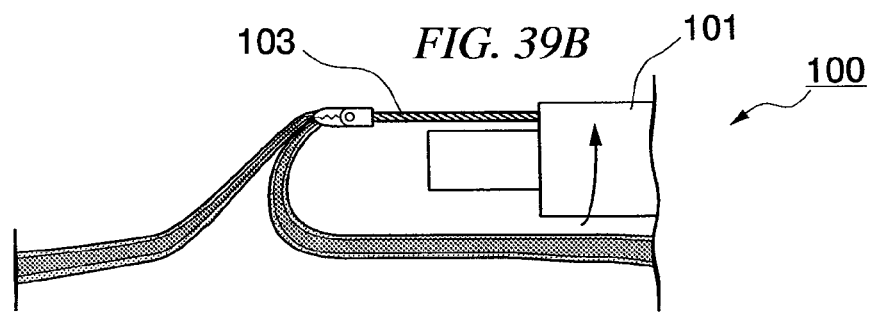
Figure 39C:
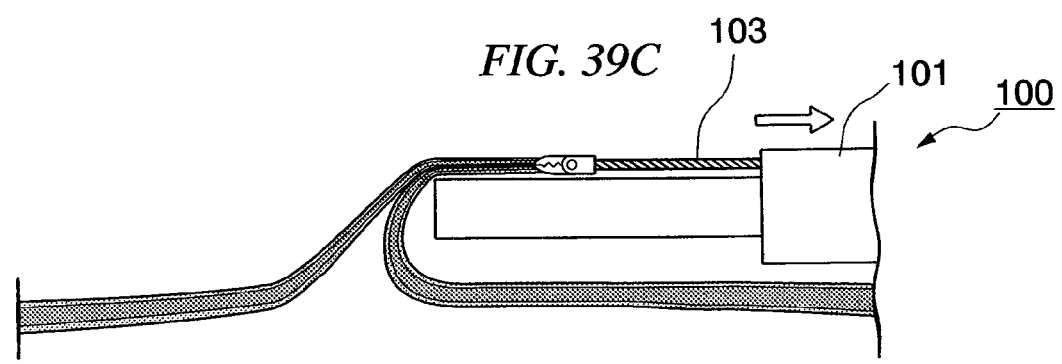

FIGS. 38 to 39C show another modified example of the device for endoscopically lifting the living tissue in the vicinity of the diseased tissue X. A device 100 shown here has an outer sheath 101 having the endoscope S inserted therethrough and a channel 102 inserted through the outer sheath 101. A lift instrument 103, for example, a grasping forceps inserted through the channel 102 is capable of extending or retracting therethrough. In addition, the outer sheath 101 itself is extendable and retractable, and is rotatable around the axial line.

According to the device 100 as shown in FIG. 39A, the outer sheath 101 is operated to be rotated in advance, and the lift instrument 103 is disposed at a lower position close to the living tissue. Subsequently, a predetermined site of the living tissue is grasped with the lift instrument 103 while observing with the endoscope. The outer sheath 101 in this state as shown in FIG. 39B is rotated by 180 degrees, and then, the lift instrument 103 is positioned upward to be separated from the living tissue. Accordingly, the grasped site of the living tissue is lifted. Subsequently, as shown in FIG. 39C, the living tissue can be further lifted by drawing the lift instrument 103 together with the outer sheath 101 proximally.

MODIFIED EXAMPLE 10

Figure 40:
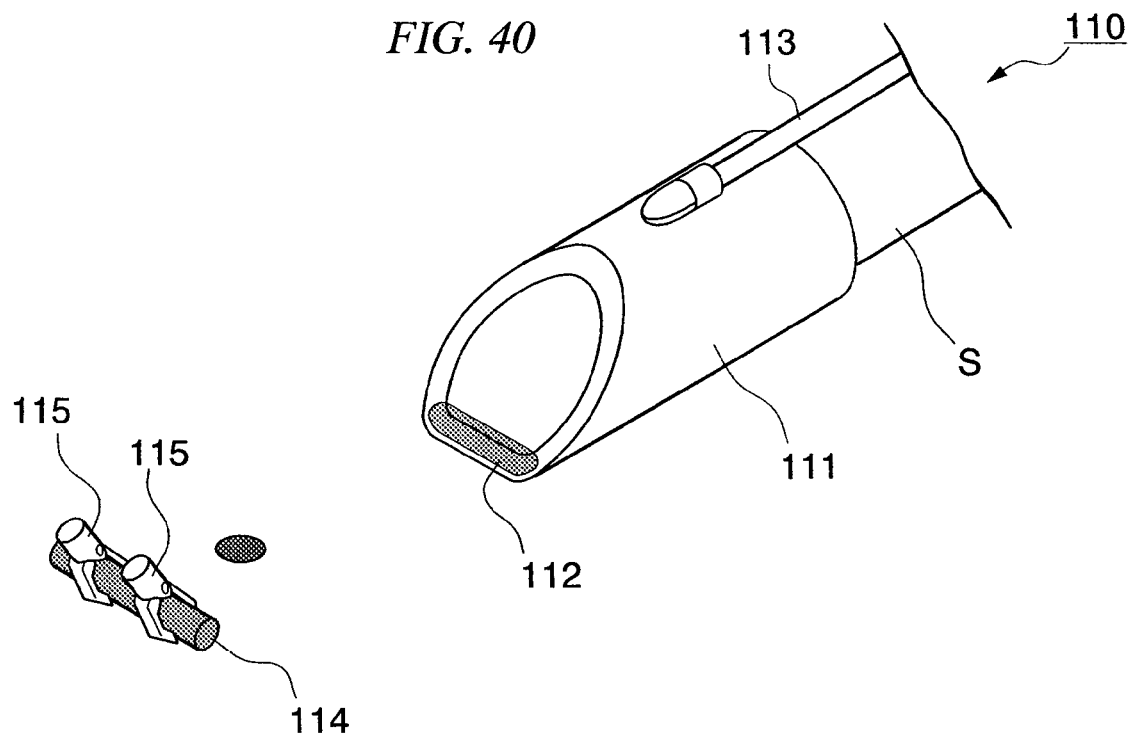
FIGS. 40 to 42 show another modified example of the device for carrying out the endoscopic surgical operation method of the present invention.
Figure 41:
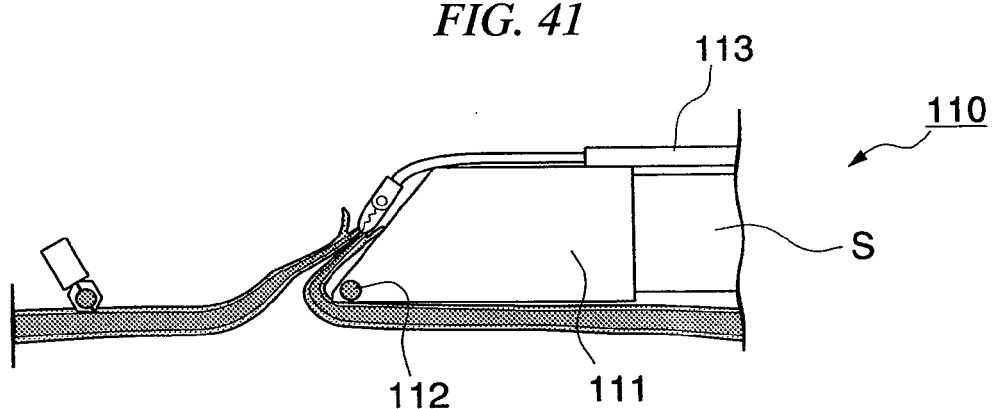
Figure 42:
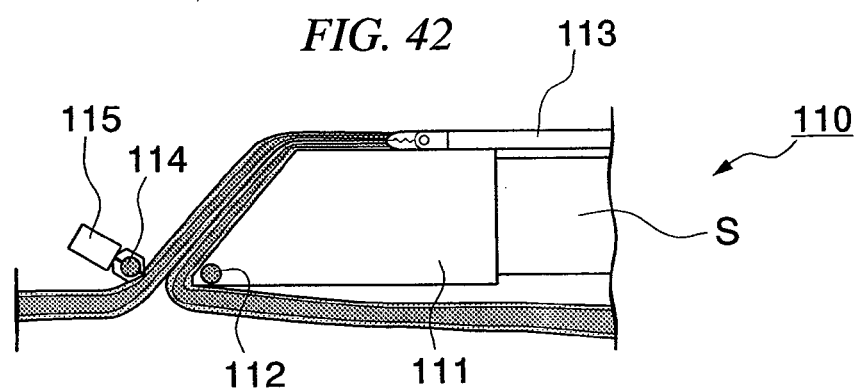
Figure 43:
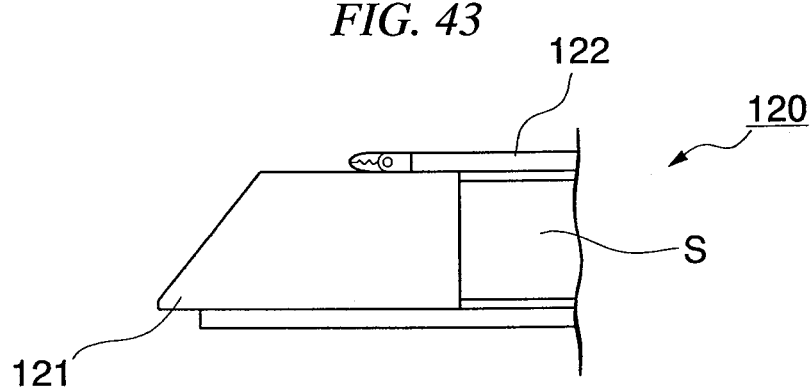
FIGS. 43 to 46 show another modified example of the device for carrying out the endoscopic surgical operation method of the present invention.

FIGS. 40 to 42 show another modified example of the device for proximally drawing an endoscopically-lifted living tissue in the vicinity of the diseased tissue X.

A device 110 shown here has a cap 111 fitting onto the distal end of the endoscope S; and a magnet 112 attached to a lower end of the cap 111. An externally-attachable lift instrument 113, for example, a grasping forceps or the like capable of extending or retracting is attached to an upper section of the cap 111. In addition, the device 110 is provided with a cap 111; a magnet 112 attached to the lower end of the cap 111; and a magnet 114 used together with the magnet 112 for fixing the living tissue. The magnet 114 for fixing the living tissue is fixed onto the diseased tissue or the living tissue therearound in advance with a clip 115 or with other retaining instruments.

According to the device 110, as shown in FIG. 41, the predetermined site of the living tissue is grasped with the lift instrument 113 while observing with the endoscope S, and then, this state of the lift instrument 113 is drawn proximally. Accordingly, the living tissue is supposed to be lifted, and this state of magnet 114 for fixing the living tissue fixed to the predetermined site of the living tissue approaches the magnet 112 of the lower end of the cap 111 in advance; thus, the magnet 114 is attracted by the magnet 112. The living tissue which is located distally relative to the distal end of the cap is drawn proximally in accordance with the movement of this state of the magnet 114 for fixing the living tissue.

MODIFIED EXAMPLE 11

FIGS. 43 to 46 show another modified example of the device for drawing the endoscopically-lifted living tissue in the vicinity of the diseased tissue X proximally relative to the cap.

A device 120 shown here has a cap 121 fitting onto the distal end of the endoscope S; and an externally-attachable lift instrument 122, for example, a grasping forceps being capable of extending or retracting and attached on the cap 121. In addition, an externally-attachable snare 123 is attached on the bottom section of the cap 121. A predetermined length of metal bar 123a having high stiffness is assembled into the snare 123.

Figure 44:
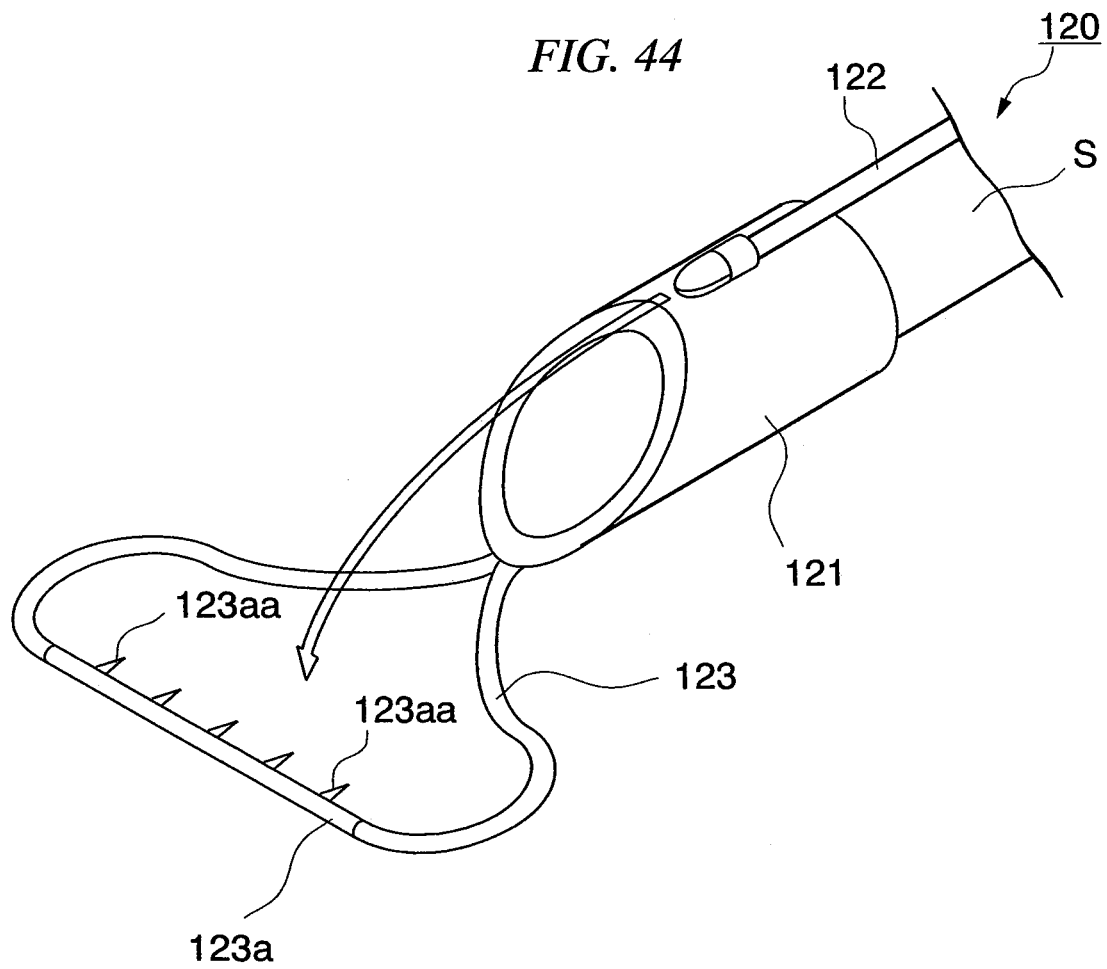
Figure 45:
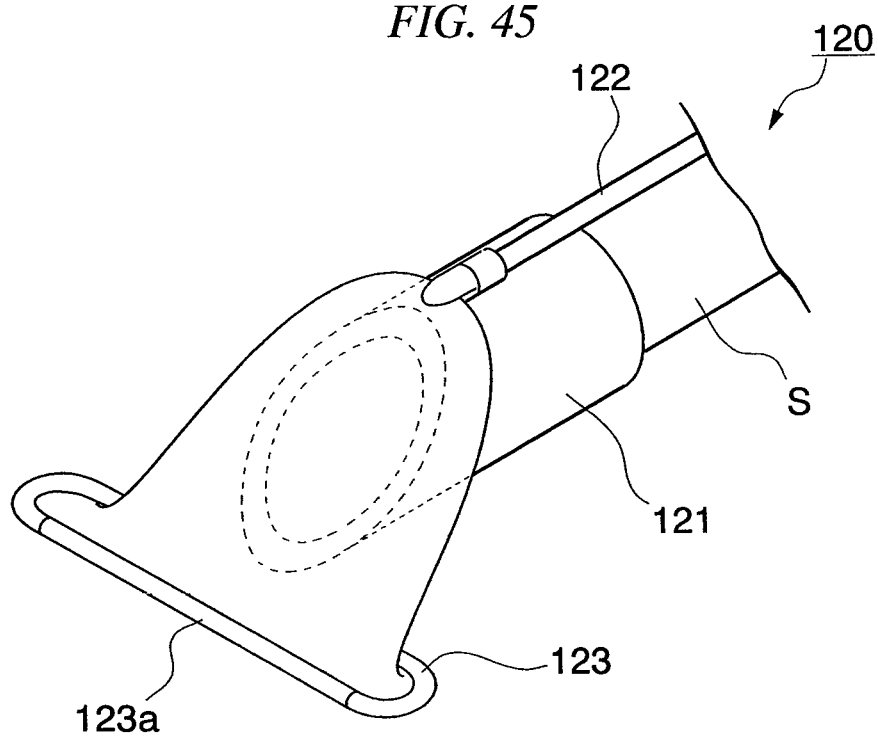
Figure 46:
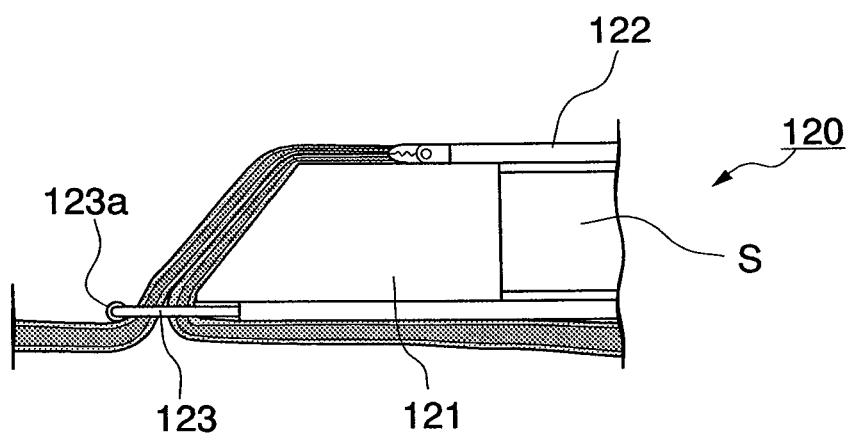

According to the device 120 as shown in FIG. 44, the snare 123 is expanded in advance, and the predetermined site of the living tissue is grasped and lifted with the lift instrument 122 passing through the device 120 to draw the living tissue further proximally. Subsequently, the snare 123 is constricted into a linear state by using the metal bar 123a as shown in FIG. 45. Constricting this state of snare 123 causes the living tissue distally located relative to the cap 121 to be drawn proximally, thereby causing the distally-located living tissue to make close contact with the proximally-located living tissue.

It should be noted that, for example, a needle-like locking section 123aa serving as a stopper for the living tissue may be attached to the metal bar 123a.

MODIFIED EXAMPLE 12

Figure 47:
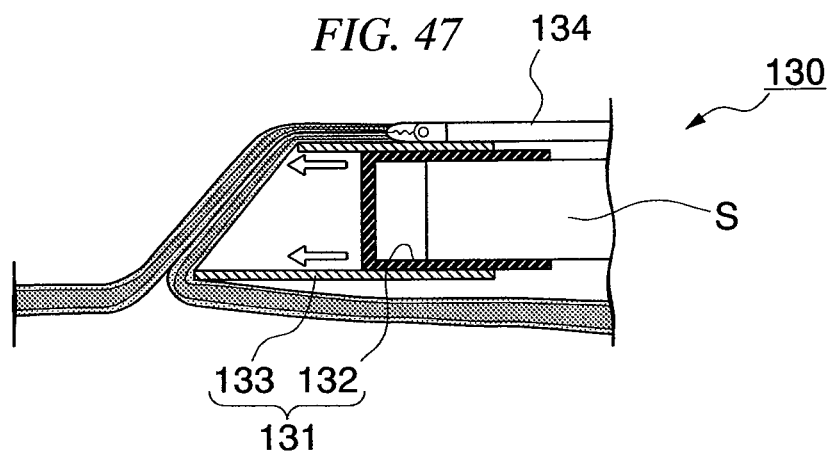
FIGS. 47 to 49 show another modified example of the device for carrying out the endoscopic surgical operation method of the present invention.

FIG. 47 shows another modified example of the device for drawing the endoscopically-lifted living tissue in the vicinity of the diseased tissue X proximally relative to the cap.

In a device 130 shown in FIG. 47, a cap 131 fitting onto the distal end of the endoscope S has two elements. That is, one is a cap main unit 132 fitting onto the distal end section of the endoscope S; and the other one is a cap tip end section 133 capable of moving in the axial line direction (the axial line direction of the endoscope) relative to the cap main unit 132. An externally-attachable lift instrument 134 capable of extending or retracting, for example, a grasping forceps or the like is attached above the cap 132. The cap tip end section 133 is operated to move by means of an operation wire, or an operation means such as an air cylinder or the like.

According to the device 130, the predetermined site of the living tissue is grasped with the lift instrument 134 while observing with the endoscope, and then, this state of the lift instrument 134 is drawn proximally. Subsequently, the proximally-located living tissue can be compressed to the distally-located living tissue by sliding the cap tip end section 133 further distally with an operation means not shown in the drawing. This results in drawing the distally-located living tissue toward the proximally-located living tissue, thereby allowing the distally-located living tissue to make close contact with the proximally-located living tissue.

MODIFIED EXAMPLE 13

Figure 48:
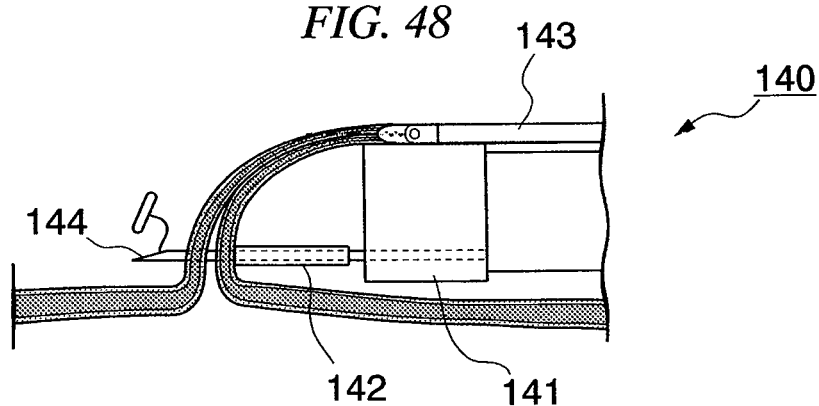
Figure 49:
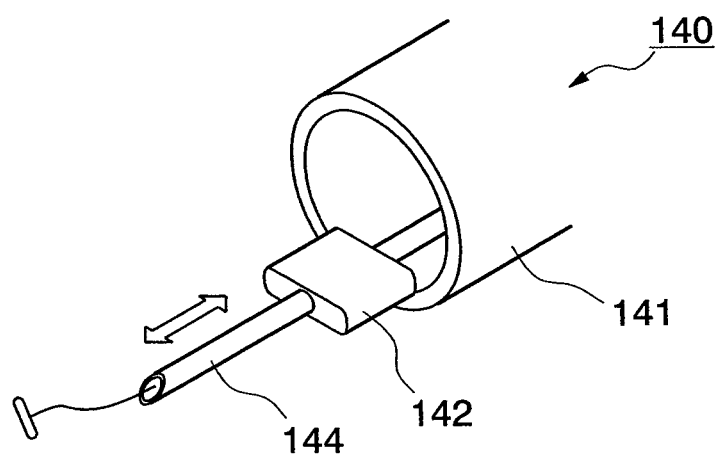

FIGS. 48 and 49 show another modified example of the device for drawing the endoscopically-lifted living tissue in the vicinity of the diseased tissue X proximally relative to the cap.

A device 140 shown here has a cap 141 fitting onto the distal end of the endoscope S; and a living-tissue-retainer 142 attached in a lower part of the cap 141 through which a puncture needle 144 of the suturing means can be inserted. The living-tissue-retainer 142 is capable of moving in the axial line direction of the endoscope S. An externally-attachable lift instrument 143, for example, a grasping forceps or the like capable of extending or retracting is attached above the cap 141.

According to the device 140, the predetermined site of the living tissue is grasped with the lift instrument 143 while observing with the endoscope S, and then, this state of the lift instrument 143 is drawn proximally. Subsequently, the distally-located living tissue and the proximally-located living tissue are penetrated with the puncture needle 144 of the suturing means projecting distally from the operation channel of the endoscope. The proximally-located living tissue can be compressed to the distally-located living tissue by moving the living-tissue-retainer 142 distally while the living tissue is penetrated with the puncture needle 144. Similarly to the aforementioned explanation, this results in drawing the distally-located living tissue toward the proximally-located living tissue, thereby allowing the distally-located living tissue to make close contact with the proximally-located living tissue.

MODIFIED EXAMPLE 14

Figure 50:
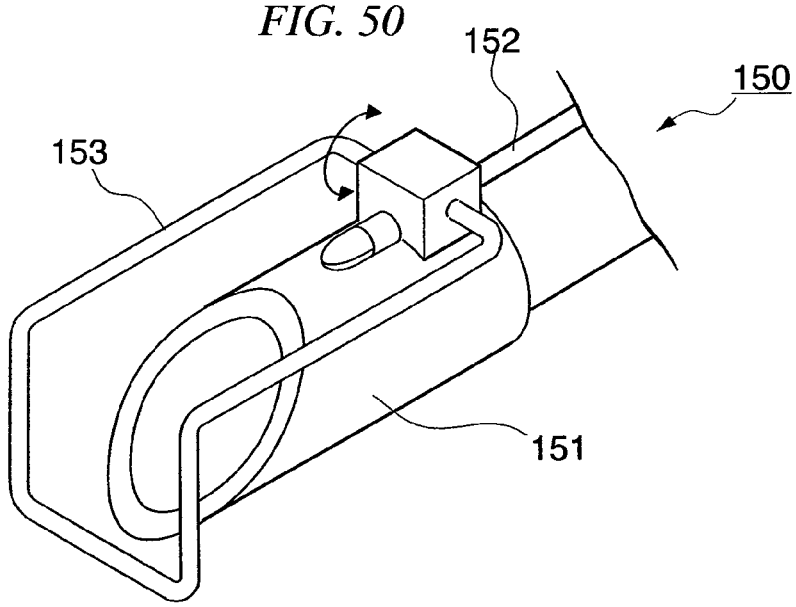
FIGS. 50 to 51B show another modified example of the device for carrying out the endoscopic surgical operation method of the present invention.
Figure 51A:
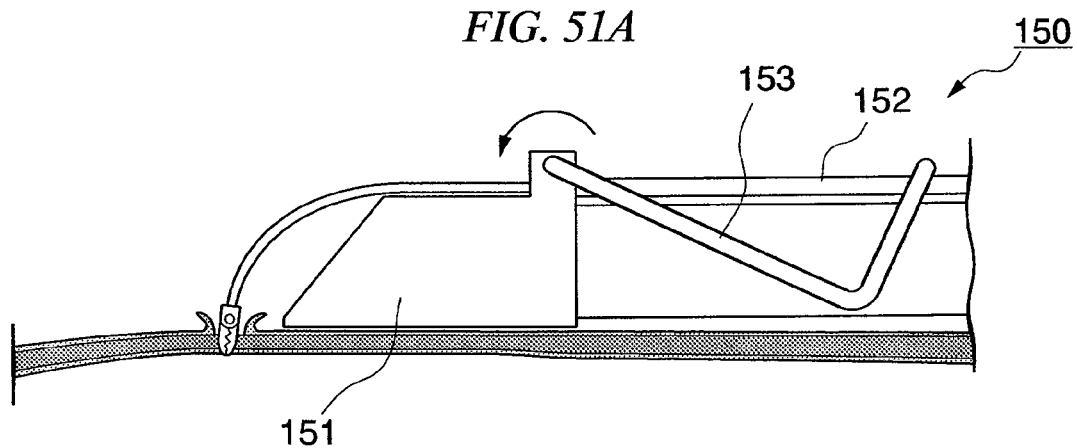
Figure 51B:
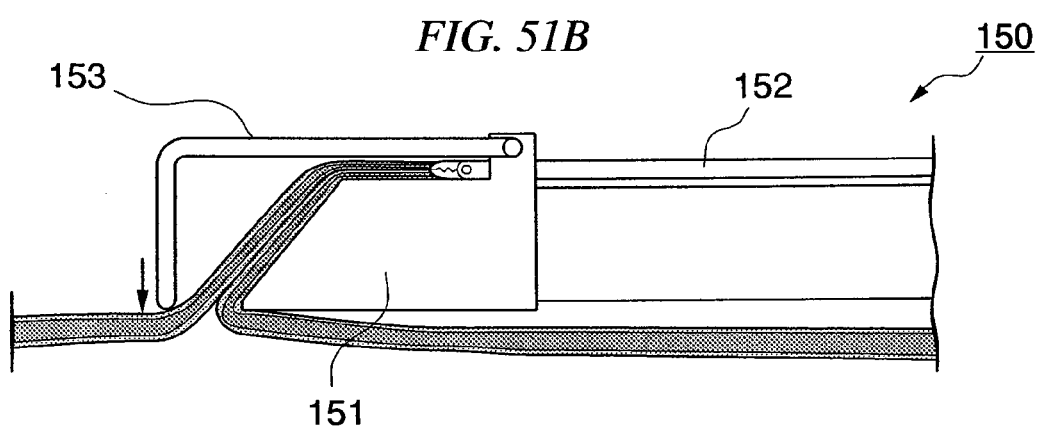

FIGS. 50 to 51B show another modified example of the device for compressing downward the endoscopically-lifted living tissue in the vicinity of the diseased tissue X.

A device 150 shown here has a cap 151 fitting onto the distal end of the endoscope S; and an externally-attachable lift instrument 152, for example, a grasping forceps being capable of extending or retracting and attached on the cap 151. In addition, an arm 153 having an L-letter shape in side view is attached on an upper section of the cap 151. The arm 153 is capable of pivoting around the axial line orthogonal to the axial line of the cap 151. The pivoting operation to the arm 153 is provided by means of a wire not shown in the drawing, an air cylinder, or a coil spring or the like.

According to the device 150, the arm 153 is pivoted proximally as shown in FIG. 51A, and the predetermined site of the living tissue is grasped with the lift instrument 152 while observing with the endoscope S, and then, this state of the lift instrument 152 is drawn proximally. While or subsequent to drawing the lift instrument 152 proximally, the arm 153 is pivoted to be disposed distally with an operation means. Since the spring or the operation wire or the like applies a force to the arm 153 having undergone the pivoting operation to pivot the arm 153 in the same direction, the distally-located living tissue is compressed downward with the arm 153. This results in preventing the distally-located living tissue from being raised inadvertently and allowing the distally-located living tissue to make close contact with the proximally-located living tissue.

MODIFIED EXAMPLE 15

FIGS. 52 to 56 show another modified example of the device for compressing downward the endoscopically-lifted living tissue in the vicinity of the diseased tissue X and drawing the living tissue proximally relative to the cap.

A device 160 shown here has a cap 161 fitting onto the distal end of the endoscope S; and an externally-attachable lift instrument 162, for example, a grasping forceps being capable of extending or retracting and attached in an upper section of the cap 161. In addition, a distally-extending guide section 163 having a guide groove 163a disposed thereinside is provided in an upper section of the cap 161. The guide section 163 has a living-tissue-retainer member 164 having an L-letter shape in side view and being capable of moving in the axial line direction of the endoscope S by means of an upper plate section 164a guided with the guide groove 163a. The movement of the living-tissue-retainer member 164 is configured to be operated with a wire or an air cylinder or the like not shown in the drawings. A through-hole 164b capable of inserting the puncture needle of the T-bar suture instrument therethrough is formed on a front surface section of the living-tissue-retainer member 164.

Figure 52:
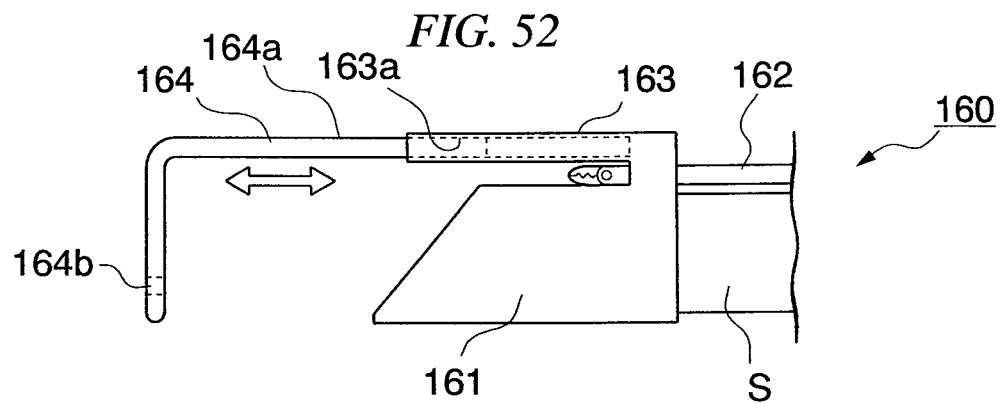
FIGS. 52 to 56 show another modified example of the device for carrying out the endoscopic surgical operation method of the present invention.
Figure 53A:
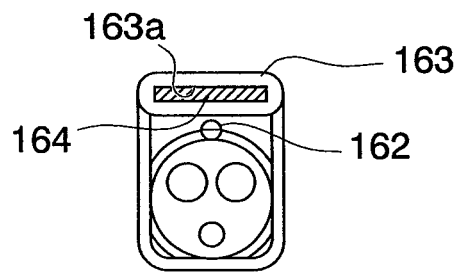
Figure 53B:
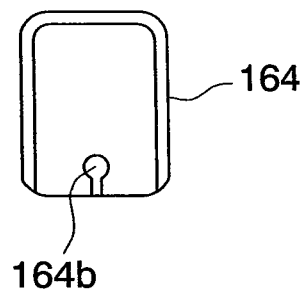
Figure 54:
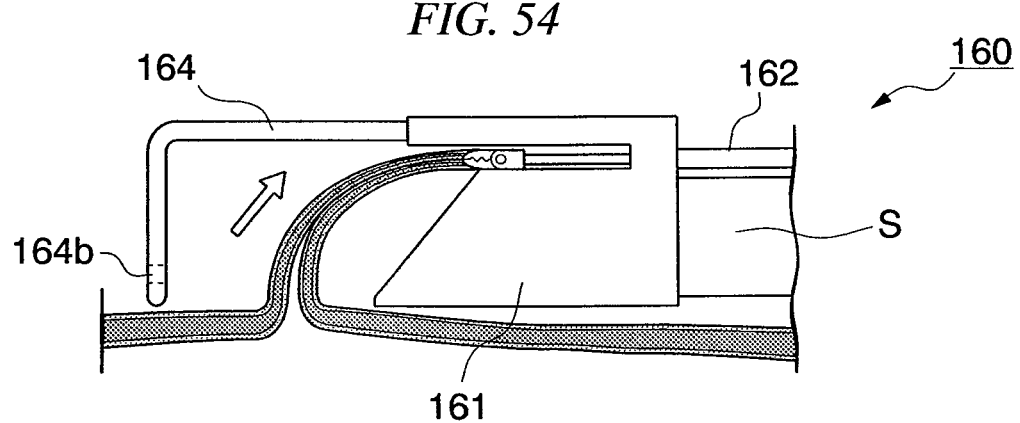

According to the device 160, the living-tissue-retainer member 164 is disposed distally as shown in FIG. 52, and the predetermined site of the living tissue is grasped with the lift instrument 162 while observing with the endoscope S, and then, this state of the lift instrument 162 is drawn proximally as shown in FIG. 54. In an attempt not to raise the distally-located living tissue, the distally-located living tissue in this state is compressed downward with the lower part of the living-tissue-retainer member 164.

Figure 55:
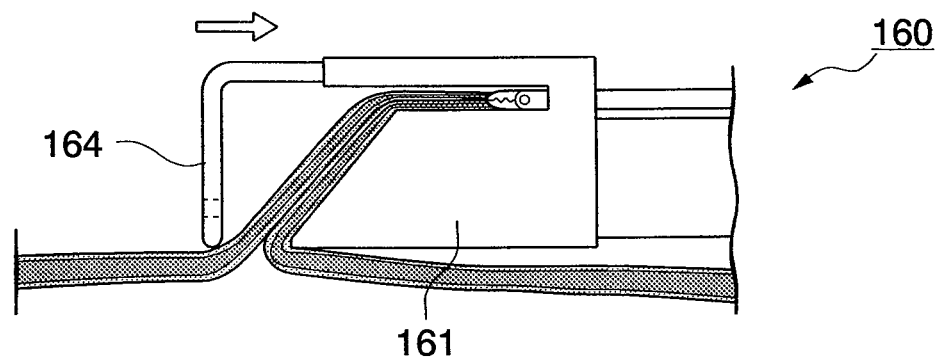

Subsequently, the living-tissue-retainer member 164 is drawn proximally as shown in FIG. 55. This allows the distally-located living tissue to be drawn proximally, thereby resulting in allowing the distally-located living tissue to make close contact with the proximally-located living tissue.

Figure 56:
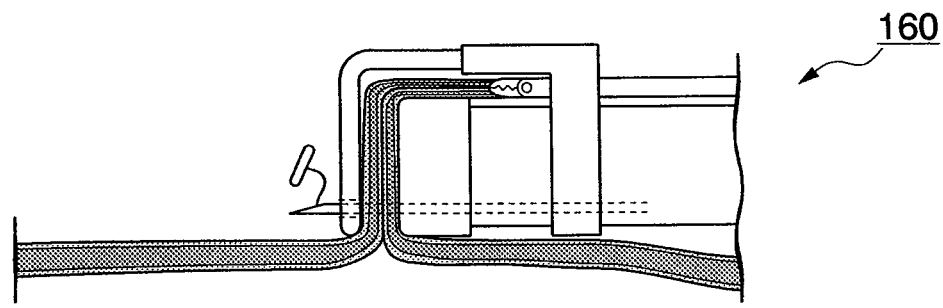

It should be noted that the distal end of the cap fitting onto the distal end of the endoscope may have an inclined shape as shown in FIGS. 52 to 55, or a flatly-cut shape as show in FIG. 56.

MODIFIED EXAMPLE 16

Figure 57:
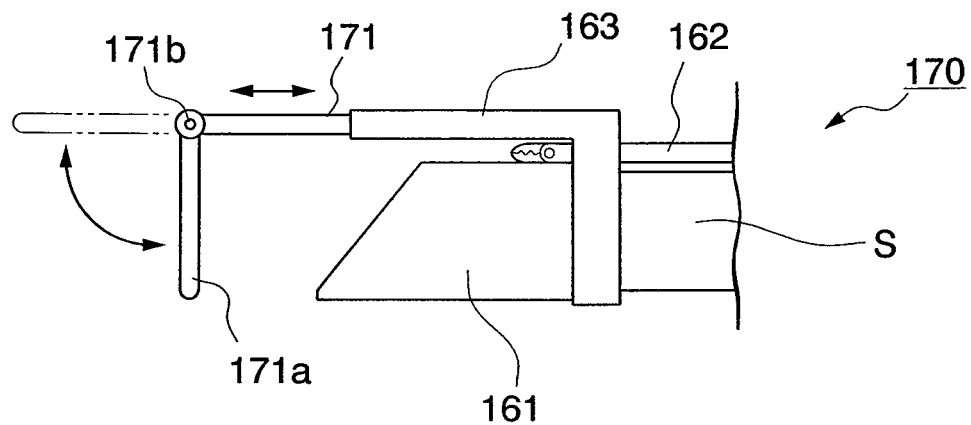
FIG. 57 shows another modified example of the device for carrying out the endoscopic surgical operation method of the present invention.

FIG. 57 shows another modified example of the device for compressing downward the endoscopically-lifted living tissue in the vicinity of the diseased tissue X and drawing the living tissue proximally relative to the cap.

In comparison with the previously-explained configurations, a device 170 shown here has a living-tissue-retainer member 171 having a distal end section 171a capable of rotating around an axial line 171b. The rotation of the distal end section 171a is configured to be operated with a wire or an air cylinder or the like not shown in the drawing. It should be noted that other sections that are the same as those of the previously-explained configurations are assigned the same reference symbols.

According to the device 170 in an attempt not to raise the distally-located living tissue, the living tissue when being lifted can be compressed downward with the upright distal end section 171a of the living-tissue-retainer member 164. Also, the distally-located living tissue can be drawn proximally by fully drawing the living-tissue-retainer member 164 or drawing the distal end section 171a of the living-tissue-retainer member 164 in a deeper angle proximally.

MODIFIED EXAMPLE 17

Figure 58:
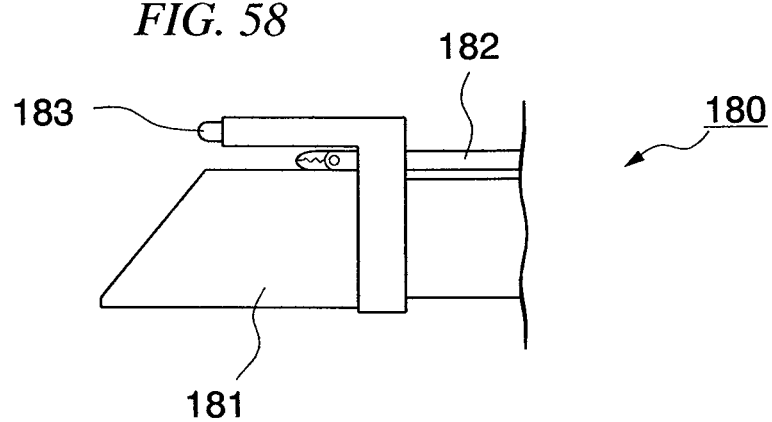
FIGS. 58 and 59 show another modified example of the device for carrying out the endoscopic surgical operation method of the present invention.
Figure 59:
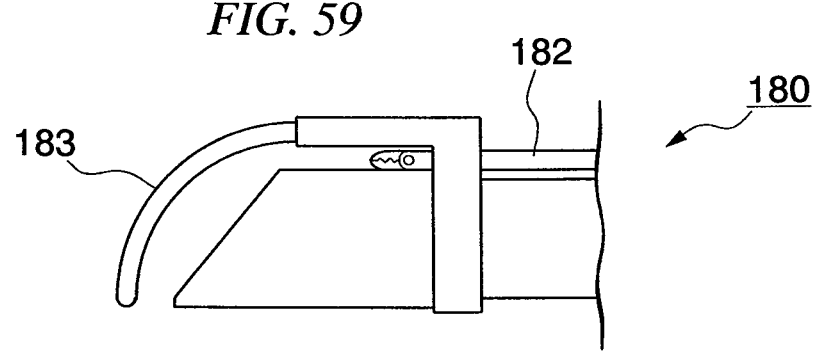

FIGS. 58 and 59 show another modified example of the device for compressing downward the endoscopically-lifted living tissue in the vicinity of the diseased tissue X and drawing the living tissue proximally relative to the cap.

A device 180 shown here has a cap 181 fitting onto the distal end of the endoscope S; and an externally-attachable lift instrument 182, for example, a grasping forceps being capable of extending or retracting and attached in an upper section of the cap 181. In addition, a plate member 183 made of a flexible material and having pre-curve is attached above the cap 181. The movement of the plate member 183 is configured to be operated with a wire or an air cylinder or the like not shown in the drawing. According to the device 180, the plate member 183 is extended in advance as shown in FIG. 59. Subsequently, the distal end of the plate member 183 bends downward by the flexible property of itself The plate member 183 is extended distally in this manner, and the predetermined site of the living tissue is grasped with the lift instrument 182 while observing with the endoscope S, and then, this state of the lift instrument 182 is drawn proximally. In an attempt not to raise the distally-located living tissue, the distally-located living tissue in this state is compressed downward with the distal end of the plate member 183.

The distally-located living tissue can be drawn proximally by lifting the living tissue and then drawing the plate member 183 proximally. This results in allowing the distally-located living tissue to make close contact with the proximally-located living tissue.

MODIFIED EXAMPLE 18

Figure 60:
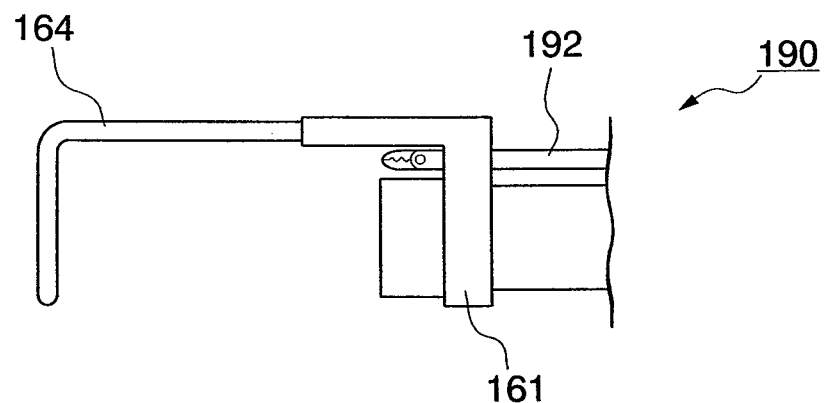
FIGS. 60 and 61 show another modified example of the device for carrying out the endoscopic surgical operation method of the present invention.
Figure 61:
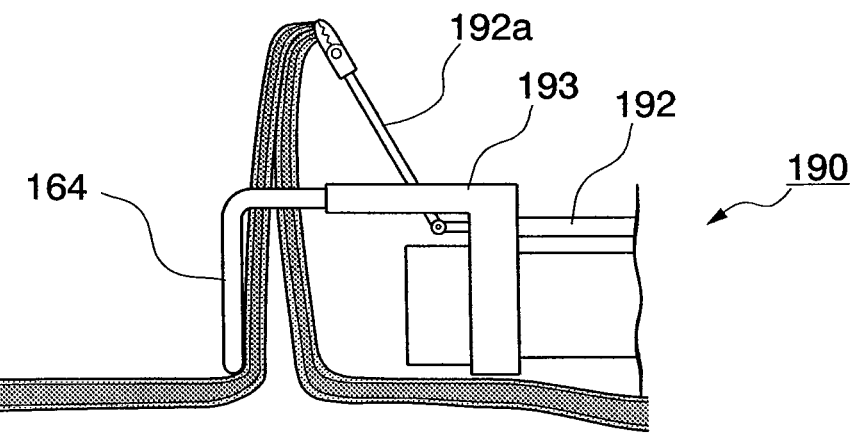

FIGS. 60 and 61 show another modified example of the device for compressing downward the endoscopically-lifted living tissue in the vicinity of the diseased tissue X and drawing the living tissue proximally relative to the cap.

A device 190 shown here is different from that shown in FIGS. 52 to 56 because a freely extendable or retractable distal end section 192*a* like a grasping forceps or the like of an externally-attachable lift instrument 192 attached above the cap 161 is capable of pivoting upward via a link 193. The pivoting angle of the distal end section 192*a* is configured to be operated with a wire or an air cylinder or the like not shown in the drawing. It should be noted that other sections that are the same as those of the previously-explained configurations shown in FIGS. 52 to 56 are assigned the same reference symbols.

As previously explained, the living-tissue-retainer member 164 having an L-letter shape in a side view can compress the distally-located living tissue downward in an attempt not to raise the distally-located living tissue and draw the distally-located living tissue distally according to the device 190. In addition, the device 190 can lift the living tissue significantly since the distal end section 192*a* of the lift instrument 192 can be lifted significantly; therefore, it is not necessary to draw the lift instrument 192 proximally.

What is claimed is:

1. An endoscopic surgical operation method comprising:
providing an endoscope, the endoscope having on its distal end a device, the device having a first body having a curved first surface and a second body having a second surface opposing the first surface, the first surface and the second surface defining a space therebetween for introduction of tissue, the space extending from a bottom of the device towards a top of the device;
providing a lift instrument;
advancing the lift instrument along the endoscope and the first surface to dispose the lift instrument to be opposed to a living tissue in the vicinity of a diseased tissue, wherein the first surface deflects the lift instrument towards the living tissue during the advancing;
grasping the living tissue using the lift instrument;
lifting the living tissue grasped by the lift instrument and drawing the living tissue and the diseased tissue into the space;
narrowing the space while the living tissue is in the space thereby causing contact between a proximal region and a distal region of the living tissue located in the space over an entirety of the living tissue within the space;
suturing the proximal region and the distal region of the living tissue positioned basal relative to the diseased tissue using a suturing means after the narrowing and the causing contact, thereby forming sutured regions that surround the diseased tissue; and
resecting the living tissue between the sutured regions and the diseased tissue endoscopically after the suturing so as to surround the diseased tissue with the resecting.

2. The endoscopic surgical operation method according to claim 1, wherein the lifting and the suturing are repeated to obtain the sutured regions in plural points.

3. The endoscopic surgical operation method according to claim 1, wherein the resecting includes resecting the living tissue in full thickness.

4. The endoscopic surgical operation method according to claim 1, wherein during the lifting, predetermined sites of the living tissue are grasped and lifted upward, and after that, the sites while being grasped and lifted are drawn proximally in an axial direction of the endoscope.

5. The endoscopic surgical operation method according to claim 1, wherein during the lifting the distal region of the living tissue lifted is lifted while being compressed with a compressing section.

6. The endoscopic surgical operation method according to claim 1, wherein, during the lifting, the distal region is drawn proximally or the proximal region is compressed distally so that the distal region of the lifted living tissue makes close contact with the proximal region of the lifted living tissue and overlaps with the proximal region.

7. The endoscopic surgical operation method according to claim 1, further comprising providing hemostasis to a bleeding region of the living tissue after the resecting.

8. The endoscopic surgical operation method according to claim 1, further comprising collecting the living tissue including the diseased tissue resected in the resecting.

9. The endoscopic surgical operation method according to claim 1, wherein, during the lifting, the living tissue is grasped at plural points, and the plural points are lifted simultaneously.

10. The endoscopic surgical operation method according to claim 1, further comprising providing markings prior to the lifting for clarifying a scope of the diseased tissue.

11. The endoscopic surgical operation method according to claim 1, further comprising providing markings, prior to the lifting, for clarifying points being subject to be grasped on the living tissue around the diseased tissue and thereafter using the markings to define an area of the living tissue which is grasped and lifted.

12. The endoscopic surgical operation method according to claim 1, wherein, during the lifting, a mucosa of the living tissue being subject to be grasped is incised, and an exposed muscle coat is grasped.

13. The endoscopic surgical operation method according to claim 1, wherein the space is formed distally relative to the endoscope.

* * * * *